(12) United States Patent
Brenneman et al.

(10) Patent No.: US 6,319,272 B1
(45) Date of Patent: Nov. 20, 2001

(54) TRANSVAGINAL ANCHOR IMPLANTATION DEVICE AND METHOD OF USE

(75) Inventors: Rodney Brenneman, San Juan Capistrano, CA (US); David Sauvageau, Methuen, MA (US); Barry N. Gellman, North Easton, MA (US); Armand A. Morin, Berkeley, MA (US)

(73) Assignee: Boston Scientific Corporation, Natick, MA (US)

( * ) Notice: Subject to any disclaimer, the term of this patent is extended or adjusted under 35 U.S.C. 154(b) by 0 days.

(21) Appl. No.: 09/537,320

(22) Filed: Mar. 29, 2000

Related U.S. Application Data

(63) Continuation of application No. 08/744,439, filed on Nov. 8, 1996, now Pat. No. 6,053,936.

(51) Int. Cl.[7] .................................................. A61B 17/04
(52) U.S. Cl. ..................... 606/232; 606/104; 606/139; 128/898
(58) Field of Search .................... 606/104, 72, 73, 606/75, 148, 139, 232, 219; 128/898

(56) References Cited

U.S. PATENT DOCUMENTS

| | | |
|---|---|---|
| 1,030,530 | 6/1912 | Palmer . |
| 1,066,025 | 7/1913 | Lieberknecht . |
| 1,179,910 | 4/1916 | Greenfield . |
| 1,417,669 | 5/1922 | Langworthy . |
| 2,200,120 | 5/1940 | Nauth ................................. 128/83 |
| 2,454,680 | 11/1948 | Stephens ........................ 248/161 |
| 2,635,238 | 4/1953 | Garland ............................. 1/49.1 |
| 2,655,921 | 10/1953 | Haboush ........................ 128/305 |
| 2,666,430 | 1/1954 | Gispert .............................. 128/83 |
| 2,707,783 | 5/1955 | Sullivan ............................ 1/49.1 |
| 3,003,155 | 10/1961 | Mielzynski et al. ................. 3/1 |
| 3,388,847 | 6/1968 | Kasulin et al. ..................... 227/19 |
| 3,551,987 | 1/1971 | Wilkinson ......................... 29/212 |
| 3,580,313 | 5/1971 | McKnight ......................... 145/46 |
| 3,593,903 | 7/1971 | Astafiev et al. ................... 227/76 |
| 3,596,656 | 8/1971 | Kaute ................................ 128/92 |
| 3,705,575 | 12/1972 | Edwards ........................ 128/1 R |
| 3,710,592 | 1/1973 | Scow ................................ 66/1 A |
| 3,744,495 | 7/1973 | Johnson ........................... 128/337 |
| 3,823,705 | 7/1974 | Trimble ........................... 128/1 R |
| 3,892,232 | 7/1975 | Neufeld ....................... 128/92 EB |
| 4,085,756 | 4/1978 | Weaver ....................... 128/303.17 |
| 4,159,716 | 7/1979 | Borchers ...................... 128/80 R |
| 4,172,458 | 10/1979 | Pereyra ........................... 128/340 |
| 4,371,124 | 2/1983 | Gifford et al. ............. 242/85.51 A |
| 4,400,833 | 8/1983 | Kurland ............................... 3/1 |

(List continued on next page.)

FOREIGN PATENT DOCUMENTS

| | | |
|---|---|---|
| 0 153 831 | 9/1985 | (EP) . |
| 0 241 240 | 10/1987 | (EP) . |
| 0 281 763 | 9/1988 | (EP) . |

(List continued on next page.)

OTHER PUBLICATIONS

Araki et al., "The Loop–Loosening Procedure For Urination Difficulties After Stamey Suspension of The Vesical Neck", J. Urology 144: 319–323 (1990).

(List continued on next page.)

Primary Examiner—Henry J. Reca
Assistant Examiner—Julian W. Woo
(74) Attorney, Agent, or Firm—Testa, Hurwitz & Thibeault, LLP

(57) ABSTRACT

Bone anchor implantation devices and methods for their use are disclosed. The bone anchor implantation devices and methods find particular application in maintaining or improving urinary continence by suspending or stabilizing the bladder neck. The devices and methods simplify procedures for suspending or stabilizing the bladder neck and further reduce their invasiveness.

14 Claims, 12 Drawing Sheets

U.S. PATENT DOCUMENTS

| | | | |
|---|---|---|---|
| 4,409,974 | 10/1983 | Freeland | 128/92 B |
| 4,414,967 | 11/1983 | Shapiro | 128/92 B |
| 4,415,111 | 11/1983 | McHarrie et al. | 227/19 |
| 4,421,112 | 12/1983 | Maines et al. | 128/92 EB |
| 4,422,567 | 12/1983 | Haynes | 227/19 |
| 4,471,769 | 9/1984 | Lockhart | 128/132 D |
| 4,527,726 | 7/1985 | Assell et al. | 227/19 |
| 4,535,768 | 8/1985 | Hourahane et al. | 128/305.1 |
| 4,537,185 | 8/1985 | Stednitz | 128/92 B |
| 4,545,374 | 10/1985 | Jacobson | 128/303 R |
| 4,549,545 | 10/1985 | Levy | 128/335 |
| 4,569,469 | 2/1986 | Mongeon et al. | 227/19 |
| 4,576,167 | 3/1986 | Noiles | 128/334 R |
| 4,606,343 | 8/1986 | Conta et al. | 128/305 |
| 4,632,100 | 12/1986 | Somers et al. | 128/92 |
| 4,633,873 | 1/1987 | Dumican et al. | 128/334 R |
| 4,635,634 | 1/1987 | Santos | 128/325 |
| 4,664,305 | 5/1987 | Blake, III et al. | 227/19 |
| 4,738,255 | 4/1988 | Goble et al. | 128/92 YF |
| 4,739,751 | 4/1988 | Sapega et al. | 128/92 V |
| 4,741,330 | 5/1988 | Hayhurst | 128/92 YR |
| 4,744,353 | 5/1988 | McFarland | 128/92 VD |
| 4,750,492 | 6/1988 | Jacobs | 128/335 |
| 4,784,126 | 11/1988 | Hourahane | 128/92 YR |
| 4,784,137 | 11/1988 | Kulik et al. | 128/334 R |
| 4,784,138 | 11/1988 | Sinnett | 128/334 R |
| 4,854,316 | 8/1989 | Davis | 128/334 R |
| 4,857,041 | 8/1989 | Annis et al. | 600/30 |
| 4,870,957 | 10/1989 | Goble et al. | 128/92 YF |
| 4,872,451 | 10/1989 | Moore et al. | 128/92 YF |
| 4,873,977 | 10/1989 | Avant et al. | 128/334 R |
| 4,883,048 | 11/1989 | Purnell et al. | 128/92 VD |
| 4,889,119 | 12/1989 | Jamiolkowski et al. | 606/220 |
| 4,898,156 | 2/1990 | Gatturna et al. | 606/72 |
| 4,899,743 | 2/1990 | Nicholson et al. | 606/74 |
| 4,926,722 | 5/1990 | Sorensen et al. | 81/487 |
| 4,938,760 | 7/1990 | Burton et al. | 600/29 |
| 4,940,467 | 7/1990 | Tronzo | 606/66 |
| 4,946,468 | 8/1990 | Li | 606/232 |
| 4,957,498 | 9/1990 | Caspari et al. | 606/146 |
| 4,960,420 | 10/1990 | Goble et al. | 606/72 |
| 4,968,315 | 11/1990 | Gatturna | 606/72 |
| 4,969,892 | 11/1990 | Burton et al. | 606/218 |
| 4,978,351 | 12/1990 | Rozas | 606/98 |
| 4,997,433 | 3/1991 | Goble et al. | 606/64 |
| 4,997,434 | 3/1991 | Seedhom et al. | 606/80 |
| 4,997,436 | 3/1991 | Oberlander | 606/142 |
| 5,002,550 | 3/1991 | Li | 606/139 |
| 5,012,822 | 5/1991 | Schwarz | 128/885 |
| 5,013,292 | 5/1991 | Lemay | 600/30 |
| 5,013,316 | 5/1991 | Goble et al. | 606/72 |
| 5,019,032 | 5/1991 | Robertson | 600/29 |
| 5,030,219 | 7/1991 | Matsen, III et al. | 606/53 |
| 5,040,715 | 8/1991 | Green et al. | 227/176 |
| 5,041,129 | 8/1991 | Hayhurst et al. | 606/232 |
| 5,046,513 | 9/1991 | Gatturna et al. | 128/898 |
| 5,052,607 | 10/1991 | Dutton | 227/107 |
| 5,057,112 | 10/1991 | Sherman et al. | 606/79 |
| 5,061,181 | 10/1991 | Niznick | 433/174 |
| 5,064,434 | 11/1991 | Haber | 623/11 |
| 5,078,730 | 1/1992 | Li et al. | 606/228 |
| 5,088,323 | 2/1992 | Johnson et al. | 73/290 R |
| 5,100,417 | 3/1992 | Cerier et al. | 606/139 |
| 5,102,421 | 4/1992 | Anspach, Jr. | 606/232 |
| 5,108,397 | 4/1992 | White | 606/60 |
| 5,112,337 | 5/1992 | Paulos et al. | 606/96 |
| 5,112,344 | 5/1992 | Petros | 606/148 |
| 5,116,338 | 5/1992 | Poggie et al. | 606/90 |
| 5,129,902 | 7/1992 | Goble et al. | 606/65 |
| 5,141,520 | 8/1992 | Goble et al. | 606/232 |
| 5,149,329 | 9/1992 | Richardson | 604/272 |
| 5,152,790 | 10/1992 | Rosenberg et al. | 623/13 |
| 5,156,315 | 10/1992 | Green et al. | 227/178 |
| 5,180,388 | 1/1993 | DiCarlo | 623/16 |
| 5,192,303 | 3/1993 | Gatturna et al. | 606/232 |
| 5,203,784 | 4/1993 | Ross et al. | 606/104 |
| 5,203,787 | 4/1993 | Noblitt et al. | 606/232 |
| 5,207,679 | 5/1993 | Li | 606/72 |
| 5,217,462 | 6/1993 | Asnis et al. | 606/73 |
| 5,217,486 | 6/1993 | Rice et al. | 606/232 |
| 5,224,946 | 7/1993 | Hayhurst et al. | 606/72 |
| 5,236,445 | 8/1993 | Hayhurst et al. | 606/232 |
| 5,242,457 | 9/1993 | Akopov et al. | 606/144 |
| 5,256,133 | 10/1993 | Spitz | 600/29 |
| 5,258,016 | 11/1993 | DiPoto et al. | 606/232 |
| 5,268,001 | 12/1993 | Nicholson et al. | 606/72 |
| 5,290,217 | 3/1994 | Campos | 600/37 |
| 5,328,077 | 7/1994 | Lou | 227/175 |
| 5,337,736 | 8/1994 | Reddy | 128/20 |
| 5,362,294 | 11/1994 | Seitzinger | 600/37 |
| 5,364,406 | 11/1994 | Sewell, Jr. | 606/138 |
| 5,366,479 | 11/1994 | McGarry et al. | 606/219 |
| 5,370,662 | 12/1994 | Stone et al. | 606/232 |
| 5,372,146 | 12/1994 | Branch | 128/898 |
| 5,379,933 | 1/1995 | Green et al. | 227/176 |
| 5,411,506 | 5/1995 | Goble et al. | 606/104 |
| 5,417,712 | 5/1995 | Whittaker et al. | 606/232 |
| 5,423,860 | 6/1995 | Lizardi et al. | 606/232 |
| 5,425,489 | 6/1995 | Shichman et al. | 227/108 |
| 5,437,603 | 8/1995 | Cerny et al. | 600/29 |
| 5,441,502 | 8/1995 | Bartlett | 606/104 |
| 5,441,508 | 8/1995 | Gazielly et al. | 606/151 |
| 5,443,482 | 8/1995 | Stone et al. | 606/232 |
| 5,474,543 | 12/1995 | McKay | 604/272 |
| 5,500,001 | 3/1996 | Trott | 606/232 |
| 5,501,683 | 3/1996 | Trott | 606/72 |
| 5,507,754 | 4/1996 | Green et al. | 606/139 |
| 5,507,796 | 4/1996 | Hasson | 606/148 |
| 5,520,696 | 5/1996 | Wenstrom, Jr. | 606/104 |
| 5,520,700 | 5/1996 | Beyar et al. | 606/139 |
| 5,522,843 | 6/1996 | Zang | 606/232 |
| 5,522,845 | 6/1996 | Wenstrom, Jr. | 606/232 |
| 5,527,342 | 6/1996 | Pietrzak et al. | 606/232 |
| 5,544,664 | 8/1996 | Benderev et al. | 128/898 |
| 5,571,117 | 11/1996 | Ahn | 606/139 |
| 5,573,548 | 11/1996 | Nazre et al. | 606/232 |
| 5,578,057 | 11/1996 | Wenstrom, Jr. | 606/232 |
| 5,582,188 | 12/1996 | Benderev et al. | 128/898 |
| 5,584,695 | 12/1996 | Lal Sachdeva et al. | 433/173 |
| 5,584,835 | 12/1996 | Greenfield | 606/73 |
| 5,591,163 | 1/1997 | Thompson | 606/29 |
| 5,591,207 | 1/1997 | Coleman | 606/232 |
| 5,607,432 | 3/1997 | Fucci | 606/104 |
| 5,611,515 | 3/1997 | Benderev et al. | 128/898 |
| 5,618,314 | 4/1997 | Harwin et al. | 606/232 |
| 5,620,012 | 4/1997 | Benderev et al. | 128/898 |
| 5,643,288 | 7/1997 | Thompson | 606/139 |
| 5,653,373 | 8/1997 | Green et al. | 227/175.1 |
| 5,662,654 | 9/1997 | Thompson | 606/72 |
| 5,662,658 | 9/1997 | Wenstrom, Jr. | 606/104 |
| 5,674,247 | 10/1997 | Sohn | 606/219 |
| 5,681,352 | 10/1997 | Clancy, III et al. | 606/232 |
| 5,683,418 | 11/1997 | Luscombe et al. | 606/232 |
| 5,690,649 | 11/1997 | Li | 606/139 |
| 5,690,655 | 11/1997 | Hart et al. | 606/148 |
| 5,690,677 | 11/1997 | Schmieding et al. | 606/232 |
| 5,697,931 | 12/1997 | Thompson | 606/72 |
| 5,702,397 | 12/1997 | Goble et al. | 606/72 |
| 5,702,415 | 12/1997 | Matthai et al. | 606/178 |
| 5,725,529 | 3/1998 | Nicholson et al. | 606/72 |
| 5,725,557 | 3/1998 | Gatturna et al. | 606/232 |

| | | | |
|---|---|---|---|
| 5,752,963 | 5/1998 | Allard et al. | 606/139 |
| 5,766,221 | 6/1998 | Benderev et al. | 606/232 |
| 5,782,862 | 7/1998 | Bonutti | 606/232 |
| 5,785,640 | 7/1998 | Kresch et al. | 600/29 |
| 5,807,403 | 9/1998 | Beyar et al. | 606/232 |
| 5,814,051 | 9/1998 | Wenstrom, Jr. | 606/104 |
| 5,814,071 | 9/1998 | McDevitt et al. | 606/232 |
| 5,814,072 | 9/1998 | Bonutti | 606/232 |
| 5,816,258 | 10/1998 | Jevis | 128/898 |
| 5,827,291 | 10/1998 | Fucci et al. | 606/104 |
| 5,836,315 | 11/1998 | Benderev et al. | 128/898 |
| 5,842,478 | 12/1998 | Benderev et al. | 128/898 |
| 5,849,004 | 12/1998 | Bramlet | 606/232 |
| 5,851,219 | 12/1998 | Goble et al. | 606/232 |
| 5,868,747 | 2/1999 | Ochoa et al. | 606/72 |
| 5,868,789 | 2/1999 | Huebner | 606/232 |
| 5,871,503 | 2/1999 | Bartlett | 606/232 |
| 5,934,283 | 8/1999 | Willem et al. | 128/885 |
| 5,972,000 | 10/1999 | Beyar et al. | 606/139 |
| 6,039,686 | 3/2000 | Kovac | 600/30 |
| 6,042,534 | 3/2000 | Gellman et al. | 600/30 |
| 6,042,583 | 3/2000 | Thompson et al. | 606/72 |

FOREIGN PATENT DOCUMENTS

| | | |
|---|---|---|
| 0 558 993 A2 | 9/1993 | (EP) . |
| 0 599 772 A1 | 6/1994 | (EP) . |
| 0 686 373 A1 | 12/1995 | (EP) . |
| 2718012 | 10/1995 | (FR) . |
| 2739016 | 3/1997 | (FR) . |
| 1044633 | 10/1966 | (GB) . |
| 2268690 A | 1/1994 | (GB) . |
| 6-114067 | 4/1994 | (JP) . |
| 503 271 | 4/1996 | (SE) . |
| 506 164 | 11/1997 | (SE) . |
| 89/10096 | 11/1989 | (WO) . |
| 92/16152 | 10/1992 | (WO) . |
| 93/10715 | 6/1993 | (WO) . |
| 93/19678 | 10/1993 | (WO) . |
| 95/16399 | 6/1995 | (WO) . |
| 96/06567 | 3/1996 | (WO) . |
| 97/41792 | 5/1996 | (WO) . |
| 96/25887 | 8/1996 | (WO) . |
| 96/28100 | 9/1996 | (WO) . |
| 97/06731 | 2/1997 | (WO) . |
| 97/13465 | 4/1997 | (WO) . |
| 97/30638 | 8/1997 | (WO) . |
| 97/43982 | 11/1997 | (WO) . |
| 98/12971 | 4/1998 | (WO) . |

OTHER PUBLICATIONS

Bayer, et al., "A New Approach to Primary Strengthening of Colostomy with Marlex Mesh to Prevent Paracolostomy Hernia", Surgery, Gynecology & Obstetrics 163:579–580 (1986).

Beck et al., "A 25–Year Experience With 519 Anterior Colporrhaphy Procedures, Obstetrics and Gynecology", 78: 1011–1018 (1991).

Benderev et al., "Anchor Fixation and other Modifications of Endoscopic Bladder Neck Suspension", Urology, 40(5):409–418 (1992).

Benderev et al., "A New Endoscopic Bladder Neck Suspension for the Outpatient Treatment of Stress Urinary Incontinence", (video v–40) J. Urology 149: 197A (1993).

Benderev, "A Modified Percutaneous Outpatient Bladder Neck Suspension System", The Journal of Urology, 152:2316–2320 (1994).

Blaivas et al., "Successful Pubovaginal Sling Surgery", Contemporary Urology, pp. 40–63, Jul. 1993.

Blaivas et al., "Pubovaginal Fascial Sling for the Treatment of Complicated Stress Urinary Incontinence", *The Journal of Urology*, vol. 145, pp. 1214–1218, Jun. 1991.

Cruikshank, "Reconstructive Procedures For The Gynecologic Surgeon", Am. J. Obsterics and Gynecology 168: 469–475 (1993).

DeLancey, "Structural Support of the Urethra as it Relates to Stress Urinary Incontinence: The Hammock Hypothesis", *Am.J. Obstet Gynecol*, 170:1713–1723, 1994.

Falconer et al., "Clinical Outcome and Changes in Connective Tissue Metabolism After Intravaginal Slingplasty in Stress Incontient Women", Int. Urogynecol J. 7:133–137 (1996).

Forneret, "Cost–effective treatment of female stress urinary incontinence: modified pereyra bladder neck suspension", Urology 25: 365–367 (1985).

Gittes, "No–incision pubovaginal suspension for stress incontinence", J. Urology 138: 568–570 (1987).

Hancock et al., "Transpubic Suspension for the Bladder Neck for Urinary Incontinence", The Journal of Urology, 123:667–668 (1980).

Hoffman et al., "Transvestibular Retropubic Bladder Neck Suspension: A pilot study", J. Reproductive Med. 40: 181–184 (1995).

Kovac et al., "Instruments & Methods Pubic Bone Suburethral Stabilization Sling for Recurrent Urinary Incontinence", Obstetrics & Gynecology 89:624–627 (1997).

Leach et al., "Modified Pereyra Bladder Neck Suspension After Previously Failed Anti–Incontinence Surgery", Urology XXIII(4):359–362 (1984).

Leach et al., "Percutaneous Bladder Neck Suspension", The Craft of Urologic Surgery 23(3):511–516 (1996).

Leach et al., "Bone Fixation Technique for Transvaginal Needle Suspension", Urology, XXXI(5):388–390 (1988).

Mascio, "Therapy of Urinary Stress Incontinence in Women: using Mitek® GII Anchors", Mitek® Brochure, 1993.

Mattox et al., Modification of the Miya Hook in Vaginal Colpopexy, The Journal of Reproductive Medicine, 40: 681–683 (Oct. 1995).

McGuire, "The Sling Procedure for Urinary Stress Incontinence", Profiles in Urology.

McKiel, Jr. et al., "Marshall–Marchetti Procedure Modification", The Journal of Urology, 96:737–739 (1966).

Mitchell et al., "Hook Needle and Retractor for Posterior Urethroplasty", J. Urology 42: 599–600 (1970).

Nativ et al., "Bladder Neck Suspension Using Bone Anchors for the Treatment of Female Stress Incontinence", ASAIO Journal, 204–208 (1997).

Nichols et al., "Identification of Pubourethral Ligaments and Their Role in Transvaginal Surgical Correction of Stress Incontinence", *Am. J. Obstet. Gynecol.*, vol. 115, No. 1, Jan. 1, 1973.

Pereyra, "A Simplified Surgical Procedure for the Correction of Stress Incontinence in Women", West. J. Surg. Obstetrics and Gynecology: 223–226 (1959).

Petros, "Ambulatory Surgery for Urinary Incontinence and Vaginal Prolapse", The Medical Journal of Australia 161:171–172 (1994).

Petros, "The Intravaginal Slingplasty Operation, a Minimally Invasive Technique for Cure of Urinary Incontinence in the Female", Aust. NZJ. Obstet. Gynaecol. 36(4):453–461 (1996).

Raz, "Modified Bladder Neck Suspension for Female Stress Incontinence", Urology 17: 82–85 (1981).

Richardson et al., "Treatment of Stress Urinary Incontinence Due to Paravaginal Fascial Defect", Obstetrics & Gynecology, vol. 57, No. 3, (Mar. 1981).

Robertson, "Soft tissue fixation to bone", Am. J. Sports Med. 14: 398–403 (1986).

Schaeffer et al., "Endoscopic Suspension of Vesical Neck for Urinary Incontinence", Urology XXIII(5):484–494 (1984).

Schatzker, "The Rationale of Operative Fracture Care", Springer–Verlag: Berlin, 1987, 159.

Scheuer, "The Modified Pereyra Bladder Neck Suspension Procedure", Using Mitek® GII Anchors, Mitek® Brochure (1993).

Spencer, "A comparison of Endoscopic suspension of the vescial neck with suprapubic vesicourethropexy for treatment of stress urinary incontinence", J. Urology 137: 411–415 (1987).

Stamey, "Endoscopic Suspension of the Vesical Neck for Urinary Incontinence in Females", Report on 203 Consecutive patients, Ann. Surg. 192: 465–471 (1980).

Stamey, "Endoscopic Suspension of The Vesical Neck For Urinary Incontience", Surgery, Gynecology and Obsterics 136: 547–554 (1973).

Stamey, "Endoscopic Suspension of the Vescial Neck", Surgery of Female Incontinence (Book Ch. 8) 115–132 (1986).

Webster, "Female Urinary Incontinence," *Urologic Surgery*, J.B. Lippincott Company: Philadelphia, 1983, 665–679.

Winter, "Peripubic Urethropexy for Urinary Stress Incontinence in Women", Urology XX(4):408–411 (1982).

Ulmsten et al., "Intravaginal Slingplasty (IVS): An Ambulatory Surgical Procedure for Treatment of Female Urinary Incontience", Scand. J. Urol. Nephrol, 29:75–82 (1995).

Ulmsten et al., "An Ambulatory Surgical Procedure Under Local Anestesia for Treatment of Female Urinary Incontinence", Int. Urogynecol. 7:81–86 (1996).

Zacharin, "Abdominoperineal Urethral Suspension in the Management of Recurrent Stress Incontinence of Urine—a 15-year Experience", *Obsterics& Gynecology*, vol. 62, No. 5, (Nov. 1983).

Zimmern, "A Prospective Evaluation of Four–Corner Bladder Neck Suspension for Grade 11/111 Cystocele Repair", Neurol. and Urodynamics 9: 231 (1990).

Zimmern, "Transvaginal Closure of the Bladder Neck", Seminars in Urology 4: 30–32 (1986).

TRANSVAGINAL ANCHOR IMPLANTATION DEVICE AND METHOD OF USE

CROSS-REFERENCE TO RELATED APPLICATION

This application is a continuation of U.S. Pat. application Ser. No. 08/744,439 filed on Nov. 8, 1996. U.S. Pat. No. 6,053,936.

FIELD OF THE INVENTION

The present invention relates to a bone anchor implantation device for use in maintaining or improving urinary continence.

BACKGROUND OF THE INVENTION

Urinary incontinence is a widespread problem in the United States and throughout the world. Urinary incontinence affects people of all ages and can severely impact a patient both physiologically and psychologically.

In approximately 30% of the women suffering from urinary incontinence, incontinence is caused by intrinsic sphincter deficiency (ISD), a condition in which the valves of the urethral sphincter do not properly coapt In approximately another 30% of incontinent women, incontinence is caused by hypermobility, a condition in which the muscles around the bladder relax, causing the bladder neck and proximal urethra to rotate and descend in response to increases in intraabdominal pressure. Hypermobility may be the result of pregnancy or other conditions which weaken the muscles. In an additional group of women with urinary incontinence, the condition is caused by a combination of ISD and hypermobility.

In males, urinary incontinence may be the consequence of post radical prostatectomy, which can destroy the valves of the urethral sphincter.

In addition to the conditions described above, urinary incontinence has a number of other causes, including birth defects, disease, injury, aging, and urinary tract infections.

Numerous approaches for treating urinary incontinence are available. For example, several procedures for stabilizing and/or slightly compressing the urethra so as to prevent the leakage of urine have been developed. The stabilizing or compressive force may be applied directly by sutures passing through the soft tissue surrounding the urethra or, alternatively, may be applied by means of a sling suspended by sutures. In many procedures bone anchors are inserted into the pubic bone or symphysis pubis in order to anchor the sutures to the bone. The present invention simplifies such procedures and firther reduces their invasiveness.

SUMMARY OF THE INVENTION

The present invention relates to devices and methods for inserting anchors, such as bone anchors, into a bone or tissue.

One aspect of the present invention is a bone anchor implantation device comprising an elongated member having a first end and a second end. A bone anchor is releasably engaged to the elongated member in the vicinity of the first end. A protective sheath is mounted over the bone anchor. The protective sheath is axially movable relative to the bone anchor such that the bone anchor is exposed from the sheath as the bone anchor is pressed into a bone by the elongated member.

In one embodiment of the present invention, the device for inserting a bone anchor into bone comprises a first handle and a second handle. The first handle has a releasably-attached bone anchor at a first end of the first handle. The bone anchor extends from the first handle. The second handle is adjacent to the first handle. The second handle has a cannula extending therefrom at a first end of said second handle such that the bone anchor is located within the cannula. The first and second handles are movable with respect to each other to effect extension of the bone anchor out of the cannula.

In one aspect of this embodiment, the first handle has an inserter shaft attached to the first end of the first handle. The inserter shaft has a proximal end and a distal end and is adapted to releasably engage a bone anchor. The second handle has a proximal end and a distal end and is hingedly attached to the first handle. The cannula has a proximal end, a distal end, and a central bone extending therethrough. The cannula is aligned with the inserter shaft such that the inserter shaft is inside the central bone of the cannula and is extendable and retractable therefrom.

In another aspect of this embodiment, the device further comprises a biasing member disposed between the first handle and the second handle. The biasing member applies a force biasing the first handle and the second handle apart. The biasing member may comprise a spring disposed between the first handle and the second handle.

In yet another aspect of this embodiment, the device is adapted for transvaginal insertion of a bone anchor.

The device may further comprise a locking mechanism for locking the device in a position in which the inserter shaft is fully retracted in the cannula.

In one version of the device, the locking mechanism also locks the device in a position in which the inserter shaft is fully extended from the cannula.

Preferably, the inserter shaft has a pair of longitudinal grooves therein for receiving a suture.

In a further preferred embodiment, the cannula has a pair of longitudinal slots therein for receiving a suture. Preferably, the grooves in the inserter shaft and the slots in the cannula are aligned and coextensive.

In a preferred version of the device the inserter shaft and the cannula are curved.

Alternatively, the inserter shaft and the cannula are straight.

Preferably, the inserter shaft is at an angle of approximately 90° relative to the first handle and the cannula is at an angle of approximately 90° relative to the second handle.

In one version of the device, a hinge is disposed between the proximal end of the first handle and the proximal end of the second handle.

Preferably, the distal end of the cannula has a sharp point adapted for piercing tissue.

In yet another aspect of the device, a protective cap is located at the distal end of the cannula.

Another aspect of the invention is a method for inserting a bone anchor into a bone. One stop of the method comprise positioning an inserter device against tissue overlying the bone. The inserter device has a first handle having a releasably-attached bone anchor extending therefrom at a first end of the first handle. A second handle is located adjacent to the first handle. The second handle has a cannula extending therefrom at a first end of the second handle and the bone anchor is located within the cannula. Another step of the method comprises inserting the cannula through tissue overlying the bone. A further step of the method comprises moving the first handle and the second handle with respect to each other to force the bone anchor out of the cannula and into the bone.

In one aspect of the method, the bone anchor is implanted transvaginally into the pubic bone. Preferably, the bone anchor is implanted in posterior pubic bone. In a further preferred embodiment of the method the bone anchor is implanted lateral to the symphysis pubis and cephalad to the inferior edge of the pubic bone.

Preferably, at least one bone anchor is implanted on either side of the urethra.

The method may further comprise compressing or stabilizing the bladder neck with a suture attached to the bone anchor. In addition, the method may further comprise the steps of creating an opening in the tissue between the vaginal wall and the urethra, positioning a sling in the opening, and compressing or stabilizing the bladder neck with the sling using sutures connected between the sling and the bone anchors.

In one version of the method, two bone anchors are implanted on each side of the urethra. In this version, one bone anchor on each side of the urethra may be located lateral to the symphysis pubis and cephalad to the inferior edge of the pubic bone. The second bone anchor may be located on the cephalad aspect of the ramus.

Yet another aspect of the present invention is a device for inserting a bone anchor into a bone comprising a handle, a shaft, and a bone anchor mount for releasably engaging a bone anchor. The handle has a proximal end and a distal end. The shaft has a first end and a second end. The first end of the shaft is connected to the distal end of said handle. The bone anchor mount is connected to the second end of the shaft and oriented toward the handle so that the bone anchor may be inserted by applying a retrograde force to the bone anchor.

The device may further comprise a protective sheath connected to said bone anchor mount for isolating said bone anchor from contact with tissue prior to implantation of said bone anchor into a bone.

Preferably, the shaft is hook shaped.

In one aspect of the device, the bone anchor mount comprises an outer cylinder, an inner cylinder, and a tapered bone anchor receptacle for releasably engaging a bone anchor. The inner cylinder is rigidly connected to the outer cylinder and extends proximally therefrom. The bone anchor receptacle is rigidly connected to said inner cylinder and extends proximally therefrom.

In one aspect of the device, the outer cylinder has a cavity therein.

In a further aspect of the device, the outer cylinder has a distal end and a proximal end. An annular shoulder is located at the proximal end of the outer cylinder. The inner cylinder is connected to the outer cylinder within the cavity of the outer cylinder.

In one version of the device, the protective sheath comprises a first telescoping cylinder, a second telescoping cylinder, and a spring. The first telescoping cylinder has a proximal end, a distal end and a lumen extending therethrough. A first shoulder is located at the distal end of the first telescoping cylinder and a second shoulder is located at the proximal end of the first telescoping cylinder. The second telescoping cylinder has a proximal end, a distal end and a lumen extending therethrough. A first shoulder is located at the distal end of the second telescoping cylinder and a second shoulder is located at the proximal end of the second telescoping cylinder. The first shoulder of the first telescoping cylinder engages the shoulder of the outer cylinder. The second shoulder of the first telescoping cylinder engages the first shoulder of the second telescoping cylinder. The spring is disposed between the second shoulder of the second telescoping cylinder and the outer cylinder, whereby the first and second telescoping cylinders are movable between a first position in which they are extended from the outer cylinder thereby covering the bone anchor, and a second position in which they are retracted in the cavity of the outer cylinder, thereby exposing the bone anchor.

Another aspect of the present invention is a method for inserting a bone anchor releasably engaged to a bone anchor implantation device into a bone comprising the steps of locating a bone anchor implantation site on the bone and applying a retrograde force to the bone anchor to implant the bone anchor into the bone.

Yet another aspect of the present invention is a method for inserting a bone anchor releasably engaged to a bone anchor implantation device into a bone comprising the steps of locating a bone anchor implantation site on the bone and pulling the bone anchor implantation device to implant the bone anchor into the bone. Preferably, the pulling step comprises applying a retrograde force to the bone anchor implantation device. Preferably, the locating and implanting steps are accomplished transvaginally.

Preferably, the pulling step utilizes a bone anchor implantation device comprising a handle, a shaft, and a bone anchor mount for releasably engaging a bone anchor. The handle has a proximal end and a distal end. The shaft has a first end and a second end. The first end of the shaft is connected to the distal end of said handle. The bone anchor mount is connected to the second end of the shaft and oriented toward the handle so that the bone anchor may be inserted by applying a retrograde force to the bone anchor.

DETAILED DESCRIPTION OF THE PREFERRED EMBODIMENTS

The present invention relates to a device for affixing a suture-carrying anchor to bone. It also relates to methods for improving or maintaining a patient's urinary continence in which bone anchors are inserted transvaginally into the posterior portion of the pubic bone or symphysis pubis and devices for use in such methods. As used herein, the terms "transvaginally" or "transvaginal access" refer to access through the vaginal introitus or from within the vagina, as opposed to access from the patient's abdominal side.

As will be described in more detail below, the methods and devices of the present invention drive a bone anchor with at least one suture attached thereto through the vaginal wall and into the posterior portion of the pubic bone or symphysis pubis. Preferably, at least one bone anchor is driven into the pubic bone on either side of the urethra. However, one of skill in the art will appreciate that a single bone anchor may also be used. The sutures attached to the bone anchors extend through the vaginal wall and may then be attached to the endopelvic fascia, the vaginal wall, a sling, or other material to stabilize and/or slightly compress the urethra, thereby improving or maintaining the patient's urinary continence.

TWO HANDLE BONE ANCHOR IMPLANTATION DEVICE

In one embodiment, the anchor implantation device has a first handle having an inserter shaft attached thereto. The inserter shaft is adapted to releasably engage or attach to a bone anchor. A second handle is hingedly attached to the first handle and has a cannula attached thereto. The cannula has a central bore extending therethrough. The cannula is aligned with the inserter shaft such that the inserter shaft is inside the central bore of the cannula and is extendable from and retractable in the cannula. Preferably, a biasing member is disposed between the first handle and the second and biases the first handle and the second handle apart.

Figure 1:
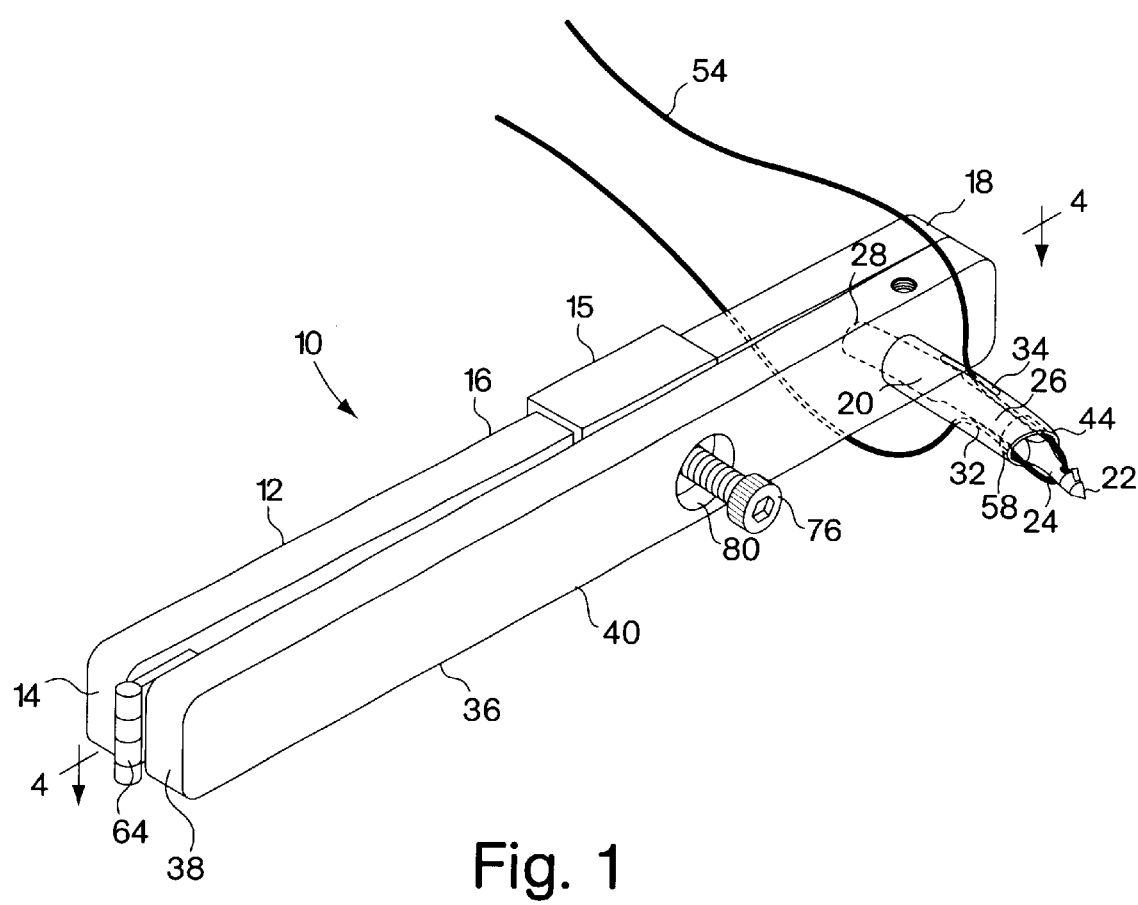
FIG. 1 is a plan view of the bone anchor implantation device.
Figure 2:
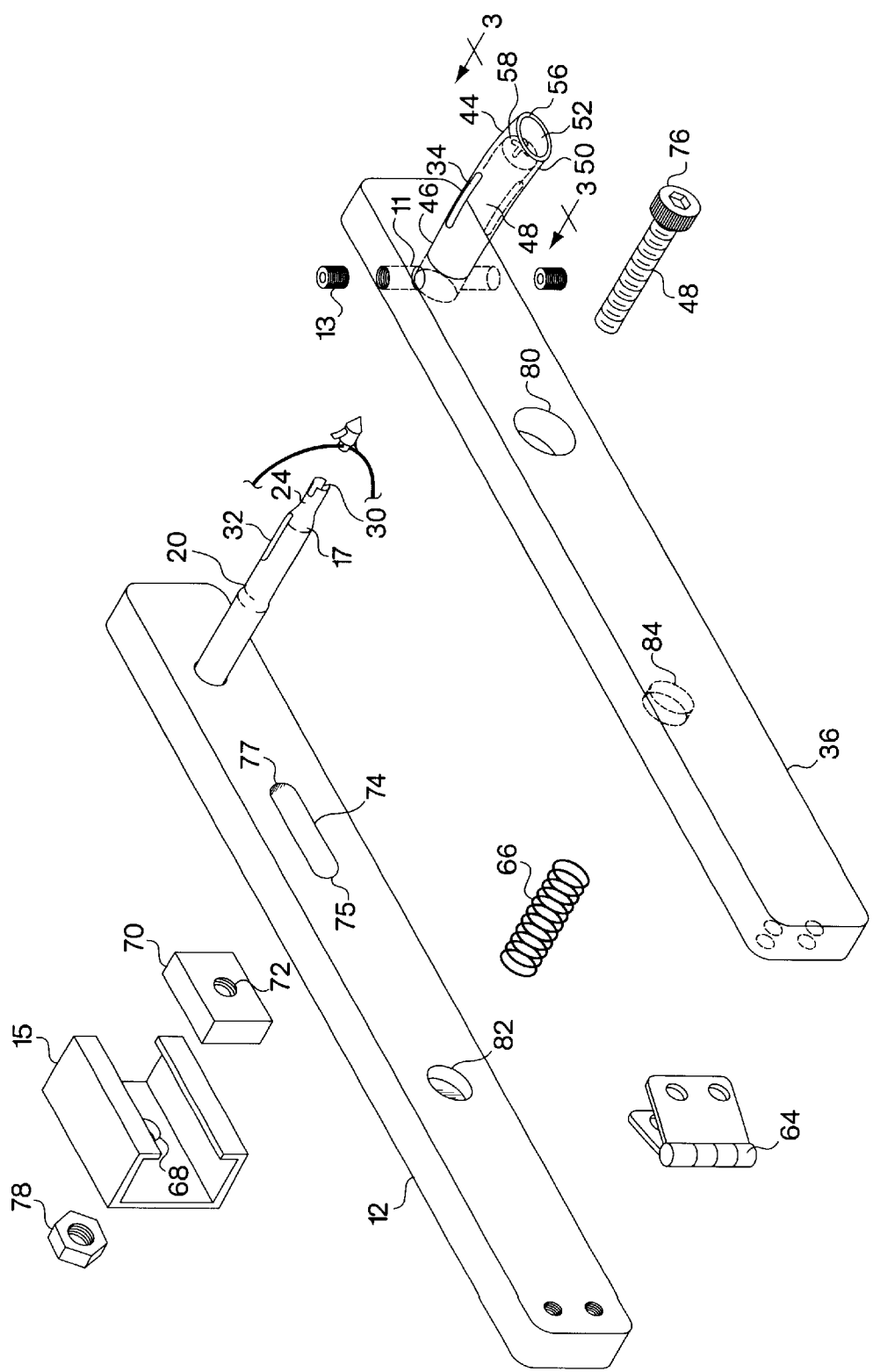
FIG. 2 is an exploded view of the anchor implantation device.

FIGS. 1 and 2 provide a plan view and an exploded view of an anchor implantation device 10 for introducing a bone anchor 22 transvaginally and driving it into the pubic bone or symphysis pubis. The device comprises a first handle 12 having a proximal end 14, a central region 16, and a distal end 18. The first handle 12 may be made of any relatively firm material, including plastic or metal. Preferably, the first handle 12 is made of plastic, aluminum, stainless steel, or titanium. However, those skilled in the art will appreciate that a wide range of other materials may also be employed.

The first handle 12 may be configured in any of a variety of shapes compatible with vaginal insertion. Preferably, the first handle 12 is rectangular. However, those skilled in the art will appreciate that a variety of configurations may be employed, such as a handle which tapers towards the distal end, and the present invention contemplates the use of any handle configuration compatible with vaginal insertion.

The dimensions of the first handle 12 are also compatible with vaginal insertion. The first handle 12 may be from about 4 inches to about 8 inches in length, about 0.25 inches to about 1.25 inches in width, and about 0.05 inches to about 0.5 inches in height. Preferably, the first handle 12 is about 5 inches to about 7 inches in length, about 0.5 inches to about 1 inch in width, and about 0.1 inches to about 0.3 inches in height. More preferably, the first handle 12 is has a length of 6 inches, a width of 0.75 inches and a height of 0.2 inches An inserter shaft 20 adapted for releasably engaging a bone anchor 22 is located near the distal end 18 of the first handle 12. A variety of bone anchors can be used. Preferably, an anchor such as that described in published PCT application WO 95/16399, entitled "Method and Apparatus for Securing Soft Tissues, Tendons, and Ligaments to Bone," filed Jun. 22, 1993, the disclosure of which is incorporated herein by reference, is used.

The inserter shaft has a distal end 24, a central region 26, and a proximal end 28. Preferably, the inserter shaft extends at an angle of about 90° from the first handle 12.

The inserter shaft 20 may be made of any of a variety of materials, including steel, stainless steel, aluminum, titanium, and plastic, but is preferably made of stainless steel. Additionally, the inserter shaft 20 may have a variety of cross sectional shapes including rectangular, hexagonal, or triangular but preferably the inserter shaft 20 has a circular cross section.

The inserter shaft 20 may be located from about 0.05 inches to about 0.5 inches from the distal end 18 of the first handle 12. Preferably, the inserter shaft 20 is located from about 0.1 inches to about 0.3 inches from the distal end 18.

More preferably, the inserter shaft 20 is located 0.2 inches from the distal end 18 of the handle.

The length of the inserter shaft 20 is consistent with transvaginal delivery of the releasable bone anchor 22. Thus, the inserter shaft 20 may be from about 0.5 inches to about 1.5 inches long. Preferably, the inserter shaft 20 is from about 0.75 inches to about 1.25 inches in length. More preferably, the inserter shaft 20 is 1 inch in length.

Preferably, the proximal end 28 and the central region 26 of the inserter shaft 20 have an equal cross sectional area, which is larger than the cross sectional area of the bone anchor 22 and distal end 24. Thus, a shoulder 17 is formed at the junction between the central region 26 of the inserter shaft and the distal region of the inserter shaft. The shoulder 17 acts as a stop which will not penetrate the cortical shell of the bone.

The diameter of the inserter shaft is dependent upon the size of the bone anchor. In embodiments in which the inserter shaft 20 is cylindrical, the diameter of the proximal end 28 and central region 26 of the inserter shaft is from about 0.1 inches to about 0.3 inches, and that of the distal end 24 is from about 0.04 inches to about 0.2 inches. Preferably, the diameter of the proximal end 28 and central region 26 of the inserter shaft is from about 0.15 inches to about 0.25 inches, and that of the distal end 24 is from about 0.07 inches to about 0.11 inches. More preferably, the diameter of the proximal end 28 and central region 26 of the inserter shaft is 0.2 inches and that of the distal end 24 is 0.09 inches.

Preferably, the inserter shaft 20 is curved as shown in FIGS. 1 and 2. As will be appreciated by those of skill in the art, the inserter shaft 20 may also be straight. In those embodiments in which the inserter shaft 20 is curved, the radius of curvature of the inserter shaft 20 is the distance between the pivot point of the hinge and the center of the inserter shaft. The radius of curvature of the inserter shaft 20 may be from about 3.5 inches to about 7.9 inches. Preferably, the radius of curvature of the inserter shaft 20 is from about 4.7 inches to about 6.9 inches. More preferably, the radius of curvature of the inserter shaft 20 is 5.8 inches.

The distal end 24 of the inserter shaft 20 is adapted to releasably engage a bone anchor 22. In one embodiment, the bone anchor 22 is housed within a notch 30 at the distal end 24 of the inserter shaft, and frictionally engages the inner wall of the distal end 24 of the inserter shaft. However, it will be appreciated by those of skill in the art that the inserter shaft 20 may releasably engage the bone anchor 22 through a variety of means other than that described above, and such means are specifically contemplated by the present invention.

The distal end 24 of the inserter shaft may be hollow or solid and has a complementary shape to the proximal end of the bone anchor 22 to permit the bone anchor 22 to frictionally engage the distal end 24 of the inserter shaft. For example, the distal end 24 of the inserter shaft and the proximal end of the bone anchor may be square, rectangular, pentagonal, triangular or hexagonal in cross section. Preferably, the distal end 24 of the inserter shaft and the proximal end of the bone anchor are cylindrical. However, those skilled in the art will appreciate that numerous shapes may be employed, and the present invention specifically contemplates any such shape.

The central region 26 of the inserter shaft has a pair of grooves 32 therein for receiving a suture 54 attached to the bone anchor as illustrated in FIGS. 1 and 2. Preferably, the grooves 32 in the inserter shaft are coextensive with slots 34 in the outer cannula and are aligned with the slots 34.

The device also comprises a second handle 36 hingedly connected to the first handle 12 and having a proximal end 38, a central region 40, and a distal end 42. The second handle 36 may be fabricated from any of the materials discussed above with regard to the first handle 12. Additionally, the second handle 36 may have any of the dimensions and shapes discussed above with regard to the first handle 12. The preferred materials, dimensions, and shapes for the second handle 36 are the same as those discussed above with regard to the first handle 12.

The second handle 36 has a cannula 44 positioned near its distal end 42 aid fixed within a bore 11 in the second handle by screws 13. The cannula 44 has a proximal end 46, a central region 48, and a distal end 50, with a central bore 52 running through its entire length. Preferably, the cannula 44 extends at an angle of about 90° from the second handle 36.

The cannula 44 may be fabricated from any of the materials described above with regard to the inserter shaft 20. Preferably, the. cannula 44 is made of stainless steel.

The cannula 44 may have any of the shapes discussed above with regard to the inserter shaft 20. Preferably, the shape of the cannula 44 is the same as that of the inserter shaft 20.

The cannula 44 is located approximately the same distance from the distal end 42 of the second handle as the inserter shaft 20 is from the distal end 18 of the first handle and the central bore 52 of the cannula has an inner diameter larger than the outer diameter of the inserter shaft 20. In this way, the inserter shaft 20 extends into the central bore in the cannula as depicted in FIG. 1. The inserter shaft 20 is extendable and retractable relative to the cannula 44.

Preferably, the cannula 44 has two oppositely disposed slots 34 therein through which the suture 54 attached to the bone anchor passes. These slots reduce the possibility of the suture 54 becoming tangled. Preferably, the slots 34 in the cannula are aligned with and coextensive with the grooves 32 in the inserter shaft.

Alternatively, the sutures can be contained within the cannula and extend out another portion of the device such as the first handle 12.

Preferably, the distal end 50 of the cannula has a sharp tip 56 to facilitate its use in piercing tissue.

As illustrated in FIGS. 1 and 2, in the embodiments in which the inserter shaft 20 is curved, the cannula 44 is preferably also curved in the same arc as the inserter shaft 20. By curving the cannula 44, the diameter of the cannula 44 can be reduced in comparison with embodiments in which the inserter shaft and the cannula are not curved. Thus, in the embodiments in which the inserter shaft 20 and cannula 44 are curved, the inner diameter of the cannula 44 is from about 0.1 inches to about 0.25 inches and the outer diameter of the cannula 44 is from about 0.14 inches to about 0.31 inches. Preferably the inner diameter of the cannula 44 is from about 0.15 inches to about 0.2 inches. In a highly preferred embodiment, the inner diameter of the cannula is 0.170 inches, the wall is about 0.02 inches, and the outer diameter is about 0.210 inches. These dimensions also apply to the devices in FIGS. 5 and 6 in which the inserter shaft and the cannula are also curved.

Figure 3:
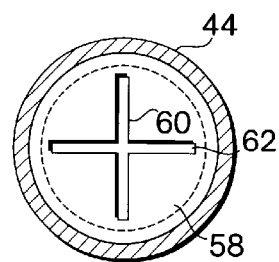
FIG. 3 is a cross-sectional view of the distal end of the cannula showing the protective cap therein taken along line 3—3 of FIG. 2.

In a preferred embodiment, the cannula 44 has a protective cap 58 inside the central bore 52 and located at the distal end 50 of the cannula, as shown in FIGS. 2 and 3. The protective cap 58 may be made of a variety of materials, such as plastic, thermoplastic elastomers, PET, PETG, rubber material, vinyl, latex, acrylic, thermoset rubbers and silicone. Preferably, the protective cap 58 is made of silicone or plastic.

The internal protective cap 58 acts to shield the bone anchor 22 from contamination, e.g., from contact with microorganisms in the vagina which could cause infection if introduced into the pubic bone during implantation of the bone anchor. In one embodiment, the protective cap 58 has a vertical slit 60 and a horizontal slit 62 therein which intersect to form a cross. Alternatively, the protective cap 58 has slits three slits which intersect to form a Y.

In one embodiment, the slits 60 and 62 penetrate entirely through the material of the protective cap 58, thereby dividing the protective cap into discrete segments. Preferably, the slits 60 and 62 are scored in the material of the protective cap 58 but do not extend entirely therethrough.

The slits 60 and 62 permit the bone anchor 22 to move through the protective cap 58 during implantation. In embodiments in which the slits 60 and 62 penetrate entirely through the material of the protective cap 58, the bone anchor 22 forces the segments of the protective cap 58 to separate as the bone anchor 22 is extended through the protective cap 58. The protective cap 58 remains in contact with the external surface of the bone anchor 22 as it is inserted into the bone, thereby shielding the bone anchor from contact with potentially infectious microorganisms in the vaginal wall.

The operation of the protective cap 58 in embodiments in which the slits 60 and 62 are scored in the protective cap is identical to that described above. However, in such embodiments, the tip of the bone anchor 22 pierces the material of the protective cap 58 as the bone anchor 22 is extended, thereby causing the protective cap 58 to separate into segments along the scores.

The proximal ends of the first and second handles, 14 and 38 respectively, are hingedly connected to permit them to move towards and away from one another. Any suitable type of hinge can be used, for example, this can be accomplished using a hinge 64 similar to that commonly found on doors as shown in FIGS. 1 and 2. Alternatively, a piece of rubber may be interposed between the first and second handles at their proximal ends 14 and 38 and secured thereto by bolts extending into holes in each of the handles. Those skilled in the art will appreciate that other means of hingedly connecting the first and second handles may be employed, and the present invention specifically contemplates embodiments in which such other hinging mechanisms are employed.

The first handle 12 and the second handle 36 are biased apart. In one embodiment, the biasing force is provided by a spring 66, as discussed below. The spring 66 can be metal, resilient polymer, pneumatically driven, or of any other suitable design. However, those skilled in the art will appreciate that a number of other structures can be employed to achieve the same biasing effect. The present invention specifically contemplates such other means of biasing the handles apart.

When sufficient force is applied to the distal ends of the first and second handles (18 and 42) to overcome the resistance of the spring, the distal ends (18 and 42) of the first and second handles move closer together. In the position in which the distal ends of the first and second handles are maximally separated, the inserter shaft 20 and bone anchor 22 thereon are fully retracted inside the cannula 44. As increasing force is applied to the handles and the distal ends approach one another, the inserter shaft 20 and bone anchor 22 thereon emerge from the distal end 50 of the cannula. At the point where the distal ends (18 and 42) of the first and second handles are touching, the inserter shaft 20 and bone anchor 22 thereon are maximally extended from the distal end 50 of the cannula.

At the point of maximum extension, the length of the inserter shaft 20 extending from the cannula 44 is from about 0.05 inches to about 0.8 inches. Preferably, at the position of maximum extension, the length of the inserter shaft 20 extending from the cannula 44 is about 0.1 inches to about 0.5 inches. More preferably, the length of the inserter shaft 20 extending from the cannula 44 at the position of maximum extension is 0.2 inches.

In the above embodiment, the bone anchor 22 is inserted in the bone by manually moving the inserter shaft 20 axially through the bore 52 in the cannula until the inserter shaft and bone anchor 22 thereon extend from the cannula 44. However, those skilled in the art will appreciate that approaches other than manually moving the inserter shaft may also be used to implant the bone anchor into the bone. For example, the bone anchor 22 can be forced into the bone by applying sufficient pneumatic pressure through the inserter shaft to eject the bone anchor from the inserter shaft with sufficient force to implant the bone anchor in the bone. Alternatively, the bone anchor may be driven into the bone by a spring mechanism.

Preferably, the device further comprises a locking mechanism for locking the device in the position in which the inserter shaft is fully retracted within the cannula in order to avoid accidental insertion of the bone anchor into tissue. As those skilled in the art will appreciate, a variety of locking structures may be used to achieve such locking.

One exemplary locking mechanism is shown in FIG. 2. The locking mechanism comprises a locking plate 15 slidably mounted over the first handle 12 and having a bore 68 therein The locking plate 15 is separated from the first handle 12 by a spacer 70 having an internally threaded bore 72 therein which is aligned with the bore 68 in the locking plate. The first handle 12 has an elongate hole 74 therein having a proximal end 75 and a distal end 77. A locking screw 76 extends through the elongate hole 74 in the first handle and the bores 72.68 in the spacer 70 and locking plate 15. The locking screw 76 is secured to the locking plate 15 by a nut 78.

Figure 4:
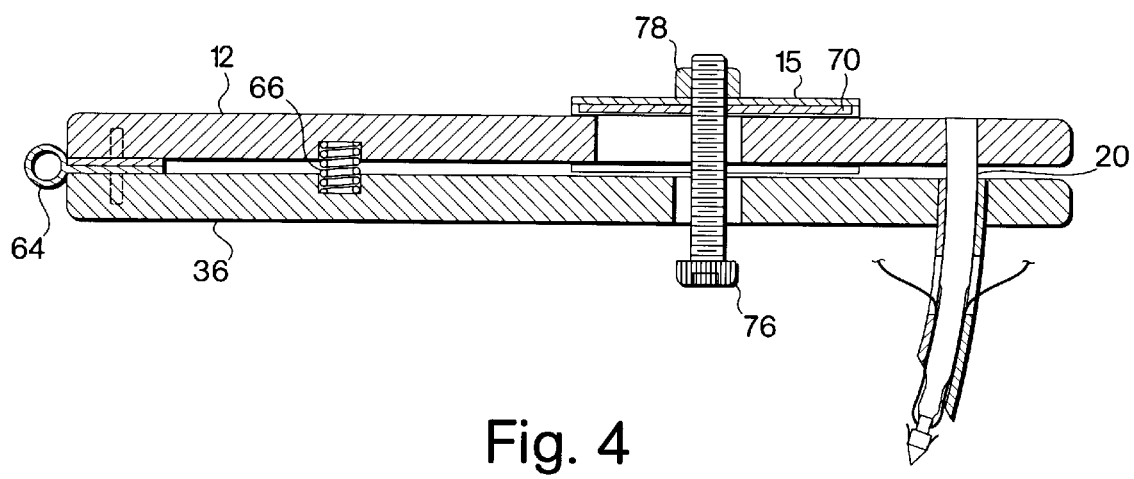
FIG. 4 is a cross-sectional view of the bone anchor implantation device of FIG. 1 taken along line 4—4 of FIG. 1.

The second handle 36 has a bore 80 therethrough having a diameter larger than that of the head of the locking screw 76. In the unlocked position, the bore 80 can be aligned with the locking screw 76 as shown in FIG. 4 thereby permitting the first handle 12 and the second handle 36 to be squeezed together such that the inserter shaft 20 extends from the cannula 44.

Figure 5:
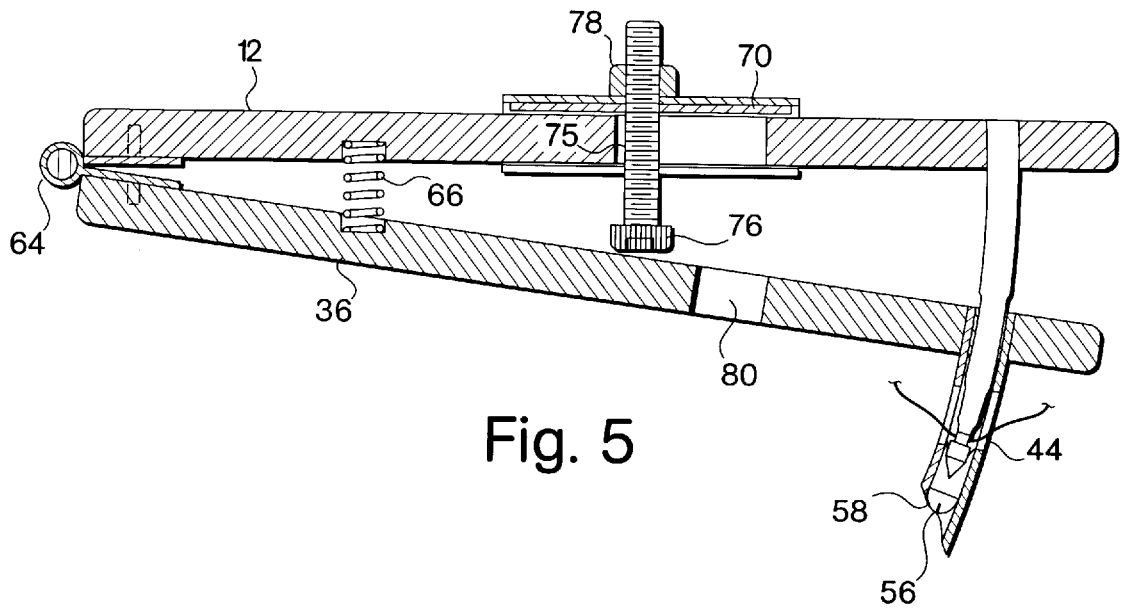
FIG. 5 is a cross-sectional view of the bone anchor implantation in its locked configuration.
Figure 6:
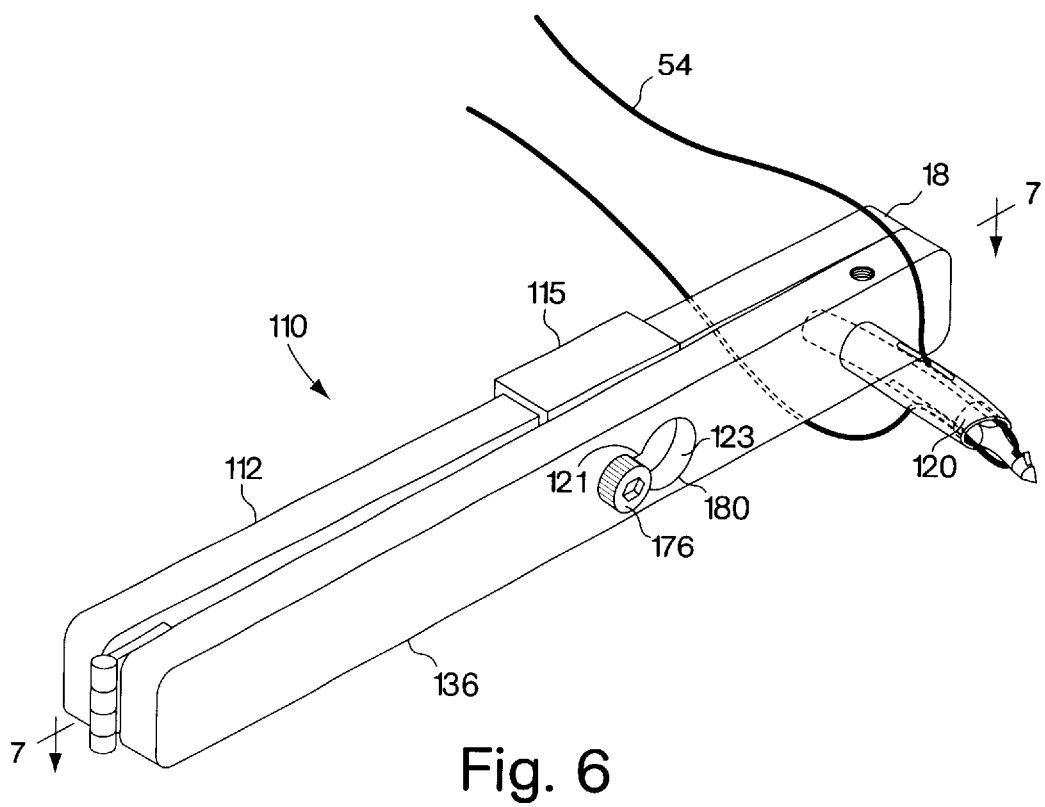
FIG. 6 is a plan view of an alternate embodiment of the bone anchor implantation device having a keyhole-shaped bore in the second handle.

As illustrated in FIG. 5, in the locked position, the locking plate 15 is positioned at the proximal end 75 of the elongate hole 74 in the first handle. In this position, the locking screw 76 is disposed between the first and second handles such that the head of the screw abuts the inner side of the second handle 36, thereby preventing the first handle 12 and the second handle 36 from being squeezed together.

Figure 7:
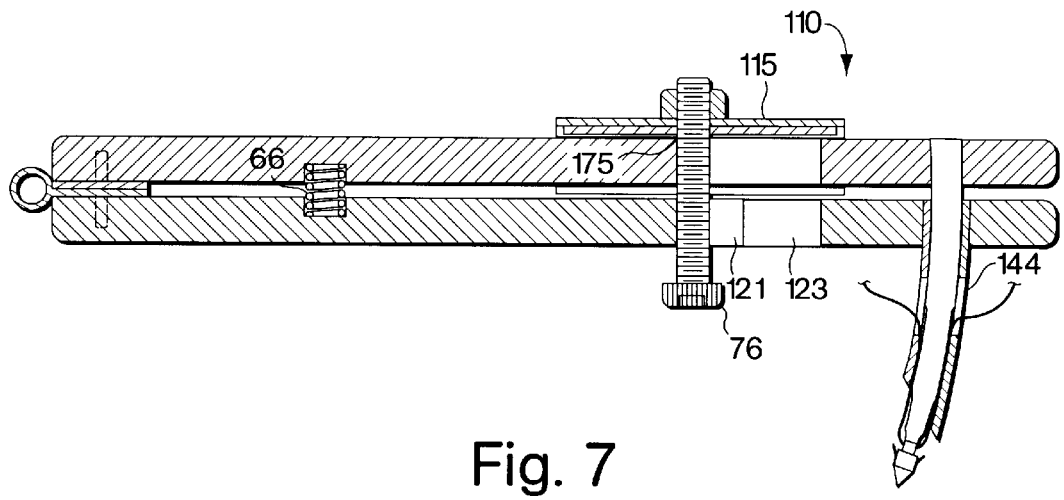
FIG. 7 is a cross-sectional view taken along line 7—7 of the alternate embodiment shown in FIG. 6 locked in the position in which the inserter shaft is fully extended from the cannula.

In an alternate embodiment, the bone anchor implantation device 110 may have a dual position lock permitting the device to be locked in a position in which the inserter shaft 120 is fully retracted within the cannula 144 or in a position in which the inserter shaft 120 is fully extended from the cannula 144. In this embodiment, illustrated in FIG. 6 the bore 180 of the second handle 136 is keyhole shaped. The narrower part 121 of the keyhole shaped bore is sufficiently narrow to prevent the head of the locking screw 176 from passing therethrough. As illustrated in FIG. 7, when the locking plate 115 is positioned at the proximal end 175 of the elongate bore in the first handle, the head of the locking screw 176 is over the narrow part 121 of the keyhole shaped aperture 180. As shown in FIG. 7, in this position the inner side of the head of locking screw 176 contacts the outer side of the second handle. The device is locked in the position in which the inserter shaft and bone anchor thereon are fully extended.

Figure 8:
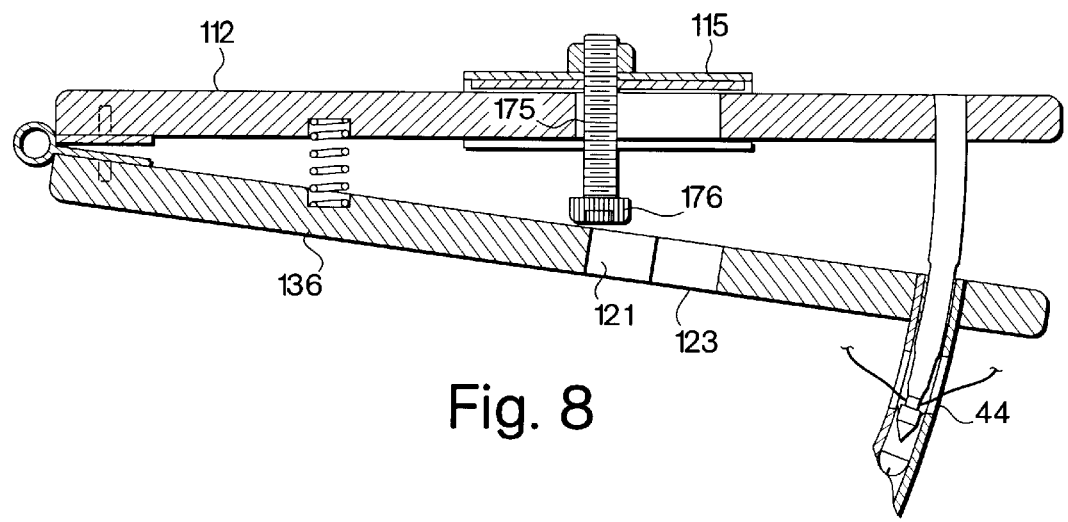
FIG. 8 is a cross-sectional view of the alternate embodiment of FIG. 6 locked in the position in which the inserter shaft is fully reacted within the cannula.

When the locking plate 115 is positioned at the distal end 177 of the elongate bore in the first handle, the head of locking screw 176 is aligned with the wide portion 123 of the keyhole shaped bore. The locking plate 115 can then be returned to the proximal end 175 of the elongate hole, such that the head of the locking screw 176 is disposed between the first handle 112 and the second handle 136 and the head of the locking screw 176 abuts the inner side of the second handle 136, as shown in FIG. 8. In this position the inserter shaft 120 is fully retracted and the first handle 112 and the second handle 136 cannot be squeezed together.

The above locking mechanisms may be used in the embodiments where the inserter shaft and cannula are straight. As those skilled in the art will appreciate, a variety of other locking structures may be used to achieve such dual position locking. Such other locking mechanisms are specifically contemplated by the present invention.

In the embodiments described above, the force biasing the two handles apart is preferably provided by a spring 66 disposed between two depressions 82 and 84 in the first handle 12 and the second handle 36. In the embodiments described above, the spring 66 is located in the central regions 16 and 40 of the first and second handles. However, those skilled in the art will appreciate that the location of the spring is not critical to the operation of the present invention. Additionally, it will be appreciated that biasing members other than a spring may be employed to bias the handles apart.

Using the present bone anchor implantation device, the bone anchor is transvaginally introduced into the pubic bone as follows.

After making an incision in the anterior vaginal wall, the endopelvic fascia is accessed using techniques well known to those of skill in the art, such as with a conventional retractor. A Foley catheter may be introduced to assist in locating the bladder neck. The bone anchor implantation device is inserted into the vaginal introitus and the first desired site for bone anchor implantation is located by digital palpation of the urethra, pubic symphysis or other anatomical landmark or other techniques known to those of ordinary skill in the art. The device is locked in the position in which the inserter shaft is fully retracted during this procedure.

Figure 9:
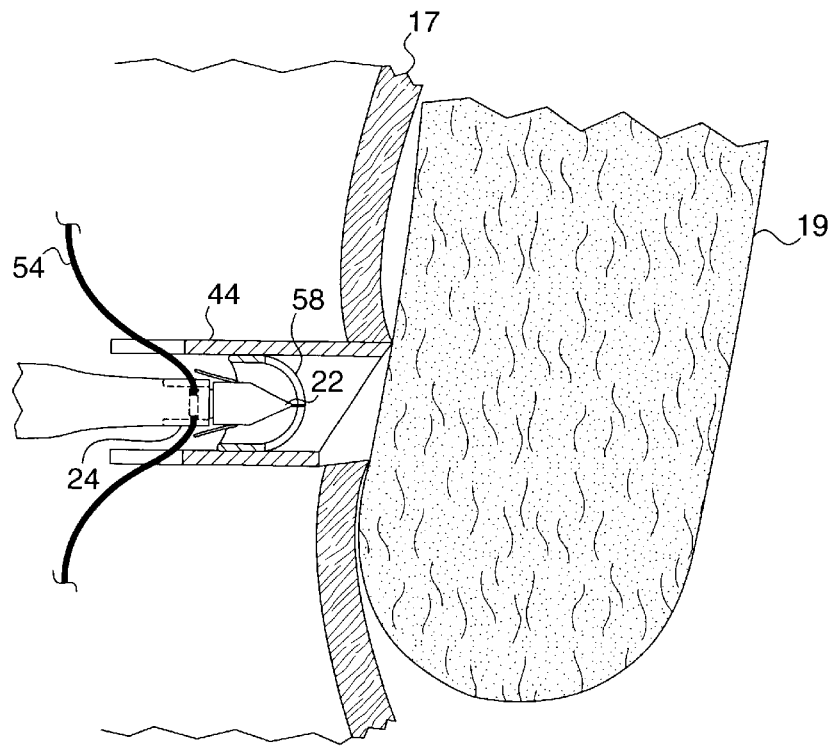
FIG. 9 is a cross-sectional view of the distal end of the inserter shaft in the cannula showing location of the bone anchor implantation site by sliding the cannula along the endopelvic fascia

Once the desired site for bone anchor implantation is located, the sharp tip 56 on the distal end of the cannula is driven through the endopelvic fascia 17. The pointed end of the cannula can also be employed to locate the desired implantation site by inserting the device into the vaginal introitus and through the incision, piercing the endopelvic fascia, and moving the cannula along the pubic bone 19 to the desired implantation site, as shown in FIG. 9.

The device is then unlocked from the position in which the inserter shaft 20 is fully retracted. In the embodiment having a single position lock, the first and second handles (12 and 36) are pressed together with enough pressure to extend the inserter shaft 20 out of the cannula 44 and drive the bone anchor 22 into the posterior portion of the bone 19. Alternatively, in the embodiment having a dual position lock, the device is locked in the position in which the inserter shaft 120 is fully extended from the cannula 144 and manual pressure is applied to drive the bone anchor 122 into the posterior portion of the pubic bone 19.

Figure 10:
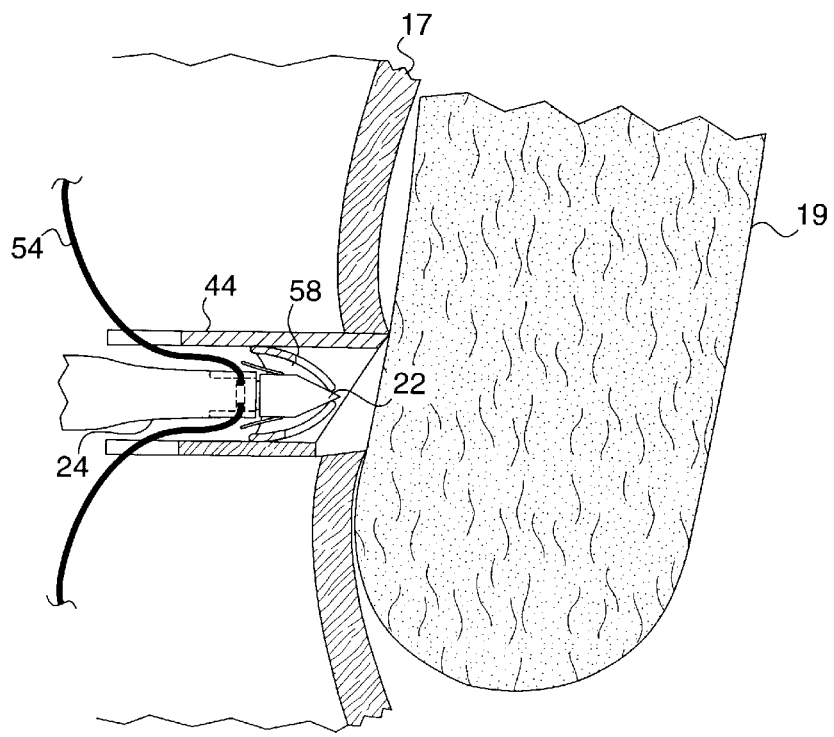
FIG. 10 is a cross-sectional view of the distal end of the inserter shaft and the cannula showing the inserter shaft penetrating the protective cap near the distal end of the cannula.

As shown in FIG. 10, when the first and second handles are squeezed towards one another, the inserter shaft moves towards the bone 19. The bone anchor 22 pierces the protective cap 58 which separates as the bone anchor 22 passes therethrough. The protective cap 58 shields the bone anchor 22 from contact with the vaginal tissue.

Figure 11:
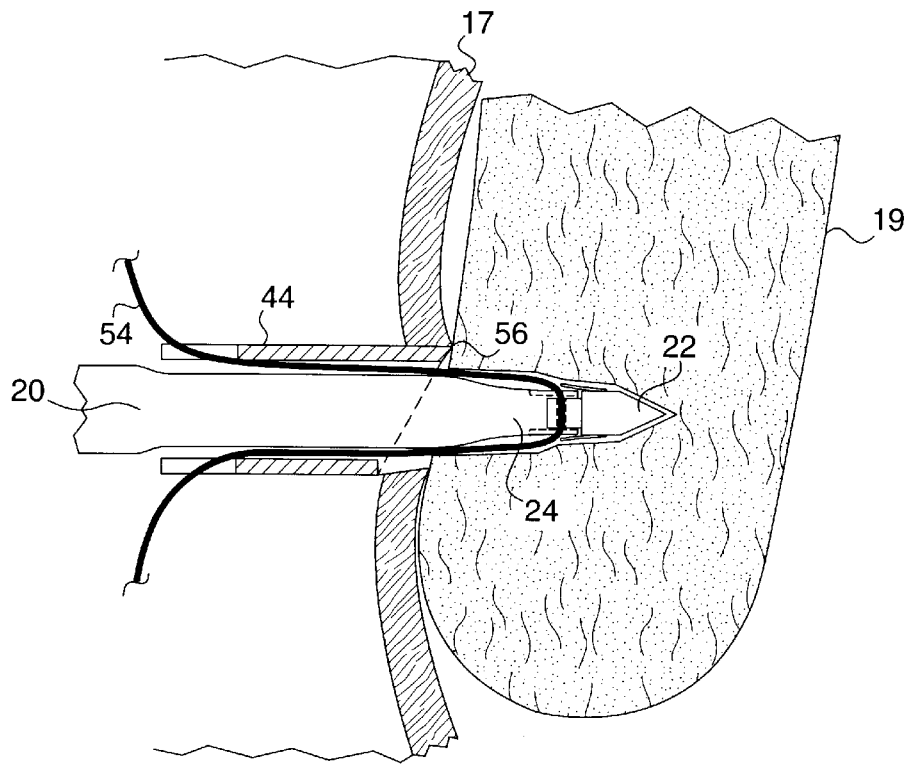
FIG. 11 is a cross-sectional view of the distal ends of the inserter shaft in the cannula showing the bone anchor being driven into the bone.

As shown in FIG. 11, when the inserter shaft 20 is extended beyond the distal tip of the cannula 56, the bone anchor contacts the bone 19 and is driven therein.

Figure 12:
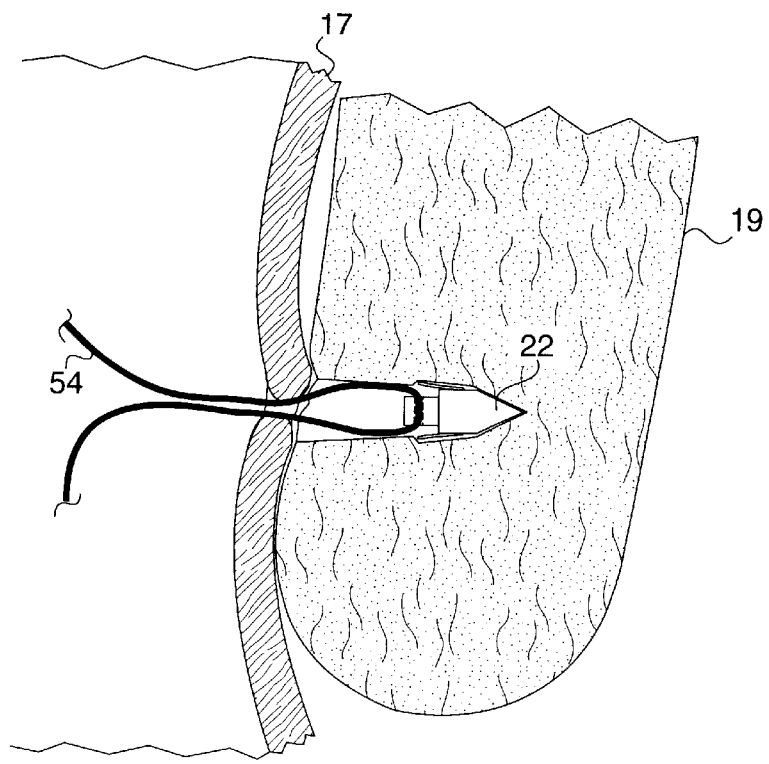
FIG. 12 shows the bone anchor with sutures extending therefrom after implantation into the bone.

The inserter shaft 20 is then retracted into the cannula 44, leaving the bone anchor 22 implanted in the bone 19 with the attached suture 54 extending through the wound in the vaginal wall and the endopelvic fascia as shown in FIG. 12.

The above site location and bone anchor implantation procedure is repeated to implant a second bone anchor on the opposite side of the urethra from the first bone anchor.

In one embodiment, the sutures are attached to a needle, looped back through the vaginal wall, and attached to tissue such as the endopelvic fascia or the vaginal wall so as to bias the tissue surrounding the urethra towards the urethra. The biasing force compresses or stabilizes the bladder neck thereby maintaining or improving urinary continence.

Alternatively, the sutures attached to the bone anchors can be attached to a sling which compresses or stabilizes the bladder neck. In such procedures, an incision is made midline to the urethra. An opening or pocket for receiving the sling is created in the tissue between the urethra and the upper vaginal wall. The bone anchor implantation device is inserted through the incision, into the pocket, and through the endopelvic fascia to contact the pubic bone. At least one bone anchor is inserted into the pubic bone on each side of the urethra. The sling is introduced into the opening or pocket and attached to the sutures. The tension on the sling provided by the sutures is adjusted to provide the appropriate biasing force to the urethra.

Example 1 describes one method of using the present bone anchor implantation device to compress or stabilize the bladder neck with sutures. It will be appreciated that the bone anchor implantation device can be used with other methods in which sutures compress or stabilize the bladder neck.

EXAMPLE 1

Compression or Stabilization of the Bladder Neck with Sutures

The bone anchor implantation device can be used in incontinence treatments in which the bladder neck is compressed or stabilized with sutures. A Foley catheter is inserted into the urethra to indicate its location. An incision is then made through the anterior vaginal wall, preferably approximately 1 cm lateral to midline and adjacent to the bladder neck. The vaginal wall is retracted to allow access to the endopelvic fascia. The bone anchor implantation device, having a bone anchor with sutures attached thereto releasably engaged with the inserter shaft, is introduced through the opening in the vaginal wall with the device locked in the position in which the inserter shaft is fully retracted within the cannula, and the sharp point is pressed through the fascia to contact the posterior pubic bone. Preferably, the anchor implantation site is located lateral to the symphysis pubis and cephalad to the inferior edge of the pubic bone. The anchor implantation site is located by palpating the inferior rim of the pubic bone and the symphysis pubis, moving laterally until the lower border of the obturator foremen is located. Preferably, the anchor is located from about 0.5 to 4 cm lateral to the symphysis pubis and from about 0.5 to 3 cm cephalad to the inferior edge. More preferably, the anchor implantation site is located approximately 1 cm lateral to the symphysis pubis and 1 cm cephalad to the inferior edge of the pubic bone. In addition, the anchor implantation site can be located on the pubic ramus.

The locking mechanism of the bone anchor implantation device is then placed in the unlocked position, and the two handles are squeezed together such that the inserter shaft is in the extended position. Alternatively, for devices having a dual position locking mechanism, the bone anchor may be exposed by locking the device in the position in which the inserter shaft is fully extended from the cannula. In either case, the anchor is driven into the pubic bone using manual pressure and opposing thumb pressure on the external pubic section if necessary.

The bone anchor implantation device is withdrawn, leaving the two free ends of the anchored suture exiting the endopelvic fascia 17. A device such as a Mayo needle is then attached to one free end of the anchored suture and a "bite of fascia" is taken adjacent to the bladder neck. Preferably, the entry and exit points of the suture are adjacent to the bladder neck approximately 0.5 cm lateral to the urethra. This step is then repeated with the other free end of the suture, and the two ends are tied together. The vaginal wall incision is then closed.

Alternatively, the entry and exit points of the suture can be made as illustrated in FIG. 13a of copending U.S. application Ser. No. 08/042,739 filed Apr. 5, 1993, issued as U.S. Pat. No. 5,611,515. the disclosure of which is incorporated herein by reference.

The above procedure is then repeated on the opposite side of the urethra to complete the bladder neck suspension. The sutures are then appropriately tensioned. Appropriate tension is confirmed using well known means such as cystoscopy or a standard Q tip test.

EXAMPLE 2

Example 2 describes use of the bone anchor implantation device in a procedure in which the bladder neck is compressed or stabilized with a sling. However, it will be appreciated that the bone anchor implantation device can be used with other methods in which the bladder neck is compressed or stabilized with a sling.

Double Anchor Placement: for Sling or Bolster Procedure

The bone anchor implantation device can also be used in incontinence treatments in which the bladder neck is compressed or stabilized using a sling. Preferably, in such procedures two bone anchors are placed on either side of the urethra. However, one of ordinary skill in the art will appreciate that one or more than two bone anchors per side can be used. The procedure is performed as follows.

A Foley catheter is inserted into the urethra to indicate its location. Starting adjacent to the bladder neck on either side of the urethra, a 1 cm incision is made through the anterior vaginal wall approximately 1 cm lateral to and parallel to the midline of the urethra. The vaginal wall is retracted to allow access to the endopelvic fascia 17. Blunt dissection is used to tunnel under the urethra and form a pocket for the sling.

The bone anchor implantation device is introduced through the opening in the vaginal wall with the device locked in the position in which the inserter shaft is fully retracted within the cannula, and the sharp point of the cannula is pressed through the fascia 17 near the distal end of the vaginal wall incision closer to the bladder neck, to contact the posterior aspect of the pubic bone. Preferably, the first anchor implant site is located lateral to the symphysis pubis and cephalad to the inferior edge of the pubic bone. More preferably, the first anchor implant site is located approximately 1 cm lateral to the symphysis pubis and 1 cm cephalad to the inferior edge of the pubic bone.

The locking mechanism of the bone anchor implantation device is then placed in the unlocked position, and the two handles are squeezed together to expose the anchor. Alternatively, for devices having a dual position locking mechanism, the bone anchor may be exposed by locking the device in the position in which the inserter shaft is fully extended from the cannula The anchor is driven into the pubic bone using manual pressure and opposing thumb pressure on the external pubic region if necessary.

The bone anchor implantation device is withdrawn leaving the two free ends of suture exiting the endopelvic fascia.

The above bone anchor implantation procedure is repeated to introduce a second anchor on the same side of the urethra as the first anchor. The second anchor implant site is located by palpating the obturator foremen in the pelvis just cephalad to the ramus. For implantation of the second anchor, the fascial tissue near the proximal end of the vaginal wall incision farther from the bladder neck is pierced. The second anchor is implanted on the superior (cephalad) aspect of the ramus.

The bone anchor implantation device is removed as before trailing the two free ends of each suture from the vaginal wall incision.

The above procedures for implantation of the first and second anchors are repeated on the opposite side of the urethra.

The sling is then positioned in the pocket under the urethra The free ends of suture from the two anchors on each side of the urethra are then tied to the corresponding corners of the sling. The sutures are then tied off with the appropriate amount of tension to suspend or stabilize the bladder neck. The vaginal wall incisions are then closed on each side.

Alternatively, the above procedure can also be utilized in techniques in which only a single bone anchor is inserted on either side of the urethra. Preferably, in such procedures the anchor implantation site is located approximately 1 cm lateral to the symphysis pubis and 1 cm cephalad to the inferior edge of the pubic bone. More preferably, the anchor implantation site is located approximately 1 cm lateral to the symphysis pubis and 1 cm cephalad to the inferior edge of the pubic bone.

Bone Anchor Implantation Device with Hooked Shaft

In another embodiment, the anchor implantation device of the present invention has a hooked shaft with a bone anchor mount for releasably engaging a bone anchor on the distal end of the shaft. This embodiment reduces the amount of force required to drive the bone anchor into the bone by utilizing the patient's body weight to provide an opposing force.

In this embodiment, the anchor implantation device comprises a handle, a hooked shaft secured to the handle and a bone anchor mount adapted to releasably engage a bone anchor attached to the distal end of the shaft. The bone anchor mount generally points toward the handle, such that the user can drive the bone anchor into the bone by simply pulling back on the handle and using the patient's body weight to provide an opposing force. Preferably, the longitudinal axis of the bone anchor mount is aligned with the longitudinal axis of the handle. Preferably, a protective sheath is attached to the bone anchor mount such that the bone anchor releasably engaged to the bone anchor mount is enclosed within the protective sheath and isolated from tissue contact during placement of the device.

Figure 13:
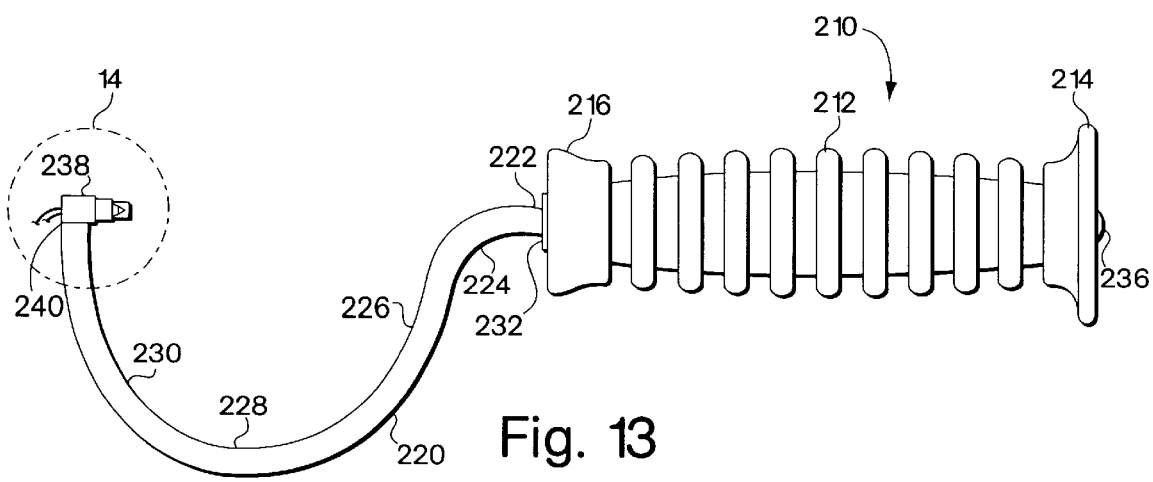
FIG. 13 is a side view of a bone anchor implantation device having a hooked shaft.

A representative anchor implantation device having a hooked shaft is shown in FIG. 13. As illustrated in FIG. 13, the anchor implantation device 210 has a handle 212 having a proximal end 214 and a distal end 216. The handle 212 may be made of a variety of materials, such as plastic or metal.

The shaft 220 may be made of a variety of materials such as stainless steel engineering plastics, fiber-bearing components, or other materials. Preferably, the shaft is made of stainless steel.

In the embodiment of the bone anchor implantation device shown in FIG. 13, shaft 220 comprises a straight proximal section 222, a first generally curved section 224 distal to the straight proximal section, a second generally curved section 226 distal to the first curved section, a third generally curved section 228 distal to the second curved section, and a fourth generally curved section 230 distal to the third curved section. However, one of skill in the art would appreciate that the shaft could also comprise a series of straight segments angled relative to one another to form a hook.

The straight proximal section 222 of the shaft 220 has an annular shoulder 232 which abuts the distal end 216 of the handle. The straight proximal section 222 passes through a lumen (not shown) extending through the handle. The proximal end of the straight proximal section 222 has a threaded bore which is adapted to receive a screw 236 which secures the shaft 220 to the handle. If desired, a washer (not shown) may be placed between the proximal end 214 of the handle and the screw 236.

While one means of securing the shaft 220 to the handle 212 was described above, those skilled in the art will appreciate that a variety of other means may be employed. For example, a plastic handle may be formed over the shaft such that the shaft is integral with the handle.

The straight proximal section 222 of the shaft 220 may be from about 3 inches to about 6 inches in length. Preferably, the straight proximal section 222 is from about 4 inches to about 5 inches in length. More preferably, the straight proximal section 222 is about 4.5 inches in length.

The handle 212 defines an axis at the proximal end of the anchor implantation device 210, and then moving distally from the handle 212 the shaft 220 first curves away from the axis of the handle and then back toward the axis of the handle 212. The distal end of the shaft 220 preferably is located in the vicinity of the axis of the handle 212. In some preferred embodiments, the shaft 220 at the distal end can be generally perpendicular to the axis of the handle or can actually be curving back toward the handle 212. Preferably, the distance from the distal end of the handle 212 to the tip of the tapered bone anchor receptacle 246 measured along the longitudinal axis of the handle 212 is about 3⅜ inches. Preferably, the distance from the distal end of the handle 212 to the distal end of the bone anchor mount 238 is about 4 inches. Preferably, the distance of a line perpendicular to the longitudinal axis of the handle 212 extending from the bottom of the third curved section 228 is about 2 inches.

Referring to FIGS. 13–16, a bone anchor mount 238 is attached to the distal end 240 of the fourth curved section 230 of the shaft 220. The bone anchor mount 238 may be oriented at an angle from about 60° to about 120° relative to the distal end 240 of the fourth curved section. Preferably, the bone anchor mount 238 is oriented at an angle from about 80° to about 100° relative to the distal end 240 of the fourth curved section. More preferably, the bone anchor mount 238 is oriented at an angle of approximately 90° relative to the distal end 240 of the fourth curved section, as illustrated in FIG. 13.

The bone anchor mount comprises an outer cylinder 242, an inner cylinder 244, and a tapered bone anchor receptacle 246 for releasably engaging a bone anchor 248. As was the case with the two handle bone anchor implantation device discussed above, a variety of bone anchors can also be used with the bone anchor implantation device having a hooked shaft. Preferably, the bone anchor used with the hooked shaft device is the bone anchor disclosed in the above incorporated published PCT application WO 95/16399.

In any event, it is preferred that the bone anchor mount 238 and the bone anchor receptacle 246 are oriented so that the bone anchor 248 is pointed in the general direction of the handle 212. In one preferred embodiment, the axis of the bone anchor 248 is generally aligned with the axis of the handle 212, with the bone anchor pointed toward the handle 212.

Figure 15:
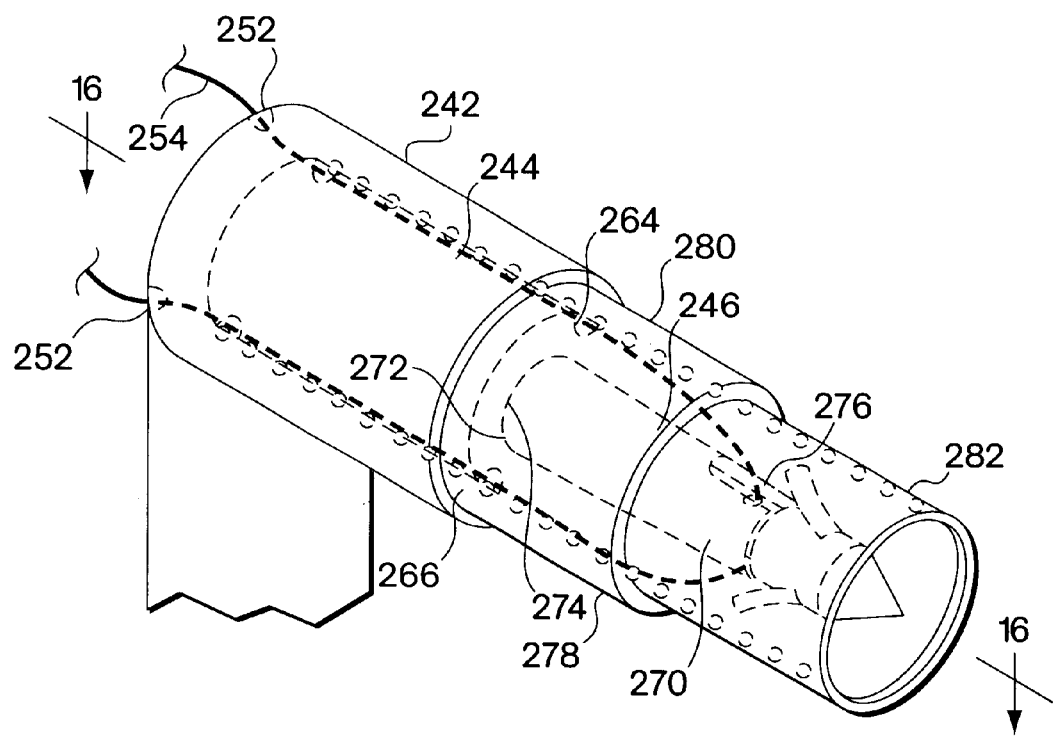
FIG. 15 is a perspective view of the bone anchor mount.

The bone anchor mount 238 may be fabricated from the same materials as the shaft 220 and may be attached to the shaft 220 by a variety of methods known to those skilled in the art, such as brazing. As best shown in FIG. 15 the distal end 250 of the outer cylinder 242 has a pair of holes 252 therein sized to accommodate a suture 254.

The outer cylinder 242 may have a diameter from about 0.18 inches to about 0.6 inches. Preferably, the outer cylinder 242 has a diameter from about 0.25 inches to about 0.5 inches. More preferably, the outer cylinder 242 has a diameter of about 0.375 inches.

Figure 16:
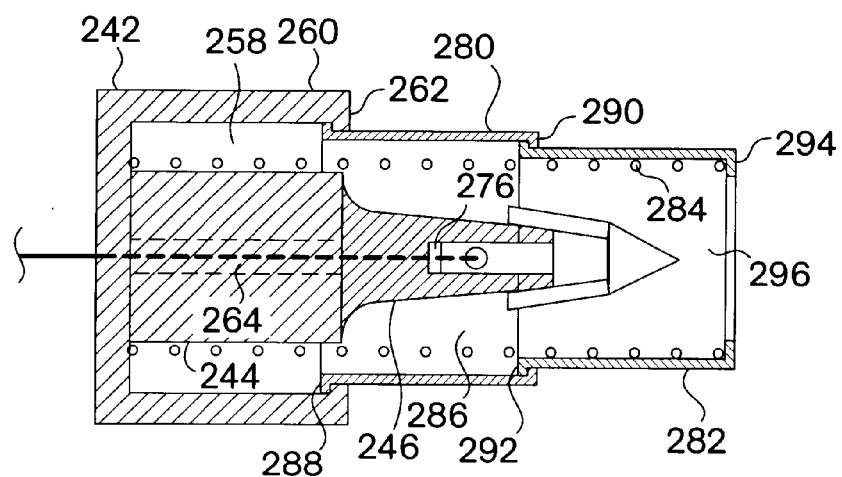
FIG. 16 is a cross sectional view of the bone anchor mount of FIG. 15 taken along line 16—16.

As best shown in the cross section of FIG. 16, the outer cylinder 242 has a cavity 258 formed therein, creating a cup in the proximal region of the outer cylinder 242. The proximal end 260 of the outer cylinder 242 has an annular shoulder 262 thereon.

The inner cylinder 244 is connected to the outer cylinder 242 and extends into the cavity 258 as best shown in FIG. 16. The inner cylinder 244 may be connected to the outer cylinder 242 in a variety of ways known to those skilled in the art. For example, the inner cylinder 244 may be fused to the outer cylinder 242. As best shown in FIG. 15, the inner cylinder 244 has grooves 264 therein adapted to accommodate the suture 254.

A tapered bone anchor receptacle 246 extends from the proximal end 266 of the inner cylinder 244. The tapered bone anchor receptacle 246 has grooves 268 therein adapted to accommodate the suture 254.

The tapered bone anchor receptacle 246 may extend from the proximal end 266 of the inner cylinder 244 by a distance of from about 0.3 inches to about 0.7 inches. Preferably, the tapered bone anchor receptacle 246 extends from the proximal end 266 of the inner cylinder 244 by a distance of from about 0.4 inches to about 0.6 inches. More preferably, the tapered bone anchor receptacle 246 extends from the proximal end 266 of the inner cylinder 244 by a distance of about 0.5 inches.

The distal end 270 of the tapered bone anchor receptacle 246 preferably has a width smaller than that of the proximal end 266 of the inner cylinder 244. This configuration produces a shoulder 272 which may serve as a depth stop to ensure that the bone anchor 248 is driven into the bone to the desired depth.

The distal end 270 of the tapered bone anchor receptacle 246 may be from about 0.08 inches to about 0.12 inches in width. Preferably, the distal end 270 of the tapered bone anchor receptacle 246 is from about 0.09 inches to about 0.110 inches in width. More preferably, the distal end of the tapered bone anchor receptacle 246 is 0.1 inches in width.

The proximal end 274 of the tapered bone anchor receptacle 246 may be from about 0.110 inches to about 0.15 inches in width. Preferably, the proximal end 274 of the tapered bone anchor receptacle 246 is from about 0.12 inches to about 0.14 inches in width. More preferably, the proximal end 274 of the tapered bone anchor receptacle 246 is 0.13 inches in width.

The proximal end 274 of the tapered bone anchor receptacle 246 may have a variety of cross sectional shapes adapted to releasably engage the bone anchor 248. For example, the proximal end 274 of the tapered bone anchor receptacle 246 may be square, rectangular, pentagonal, triangular or hexagonal in cross section.

Figure 14:
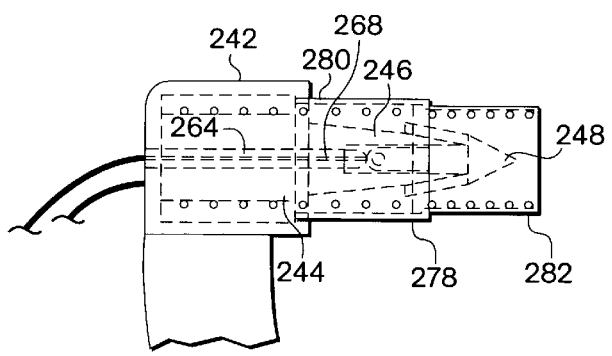
FIG. 14 is an enlarged side view of a distal portion of the bone anchor implantation device taken along line 14—14 of FIG. 13 showing the internal structure of the bone anchor mount.

As depicted in FIGS. 14–16, the tapered bone anchor receptacle 246 may have a notch 276 therein in which the bone anchor 248 is releasably seated.

Alternatively, the outer cylinder, inner cylinder, and tapered bone anchor receptacle may be a single integral component.

Preferably, the bone anchor implantation device has a protective sheath connected to the bone anchor mount which protects the point of the bone anchor from tissue contact during placement of the device and also protects the bone anchor from contacting potentially infectious microorganisms.

One embodiment of the protective sheath 278 is shown in FIGS. 13–16. In this embodiment, the protective sheath 278 comprises a first telescoping cylinder 280 and a second telescoping cylinder 282. A spring 284 biases the first telescoping cylinder 280 and the second telescoping cylinder 282 to a position in which they extend from the outer cylinder 242 and cover the bone anchor 248.

The first and second telescoping cylinders 280, 282 may be made of a variety of materials such as stainless steel or plastic. Preferably, the first and second telescoping cylinders 280, 282 are made of stainless steel.

The first telescoping cylinder 280 has a lumen 286 extending therethrough. The first telescoping 280 cylinder has a first shoulder 288 which engages shoulder 262 on the outer cylinder 242 and a second shoulder 290 which engages a first shoulder 292 on the second telescoping cylinder 282.

The second.telescoping cylinder 282 has a first shoulder 292 which engages the second shoulder 290 on the first telescoping cylinder 280 as described above. A second shoulder 294 is located at the proximal end of the second telescoping cylinder 282 and engages the spring 284. The second telescoping cylinder 282 also has a lumen 296 extending therethrough which is in fluid communication with the lumen 286 of the first telescoping cylinder 280 and the cavity 258 in the outer cylinder 242.

The inner diameter of the first telescoping cylinder 280 is slightly larger than the outer diameter of the of the second telescoping cylinder 282 such that the second telescoping cylinder 282 can retract inside the first telescoping cylinder 280. The first telescoping cylinder 280 and the second telescoping cylinder 282 can retract inside the cavity 258 of the outer cylinder 242.

The first telescoping cylinder 280 may be from about 0.2 inches to about 0.3 inches in length, with an inner diameter of from about 0.27 inches to about 0.33 inches and an outer diameter of about 0.3 inches to about 0.36 inches. Preferably, the first telescoping cylinder 280 is from about 0.23 inches to about 0.27 inches in length, with an inner diameter of from about 0.29 inches to about 0.31 inches and an outer diameter of about 0.32 inches to about 0.34 inches. More preferably, the first telescoping cylinder 280 is about 0.25 inches in length, with an inner diameter of about 0.3 inches and an outer diameter of about 0.33 inches.

The second telescoping cylinder 282 may be from about 0.2 inches to about 0.3 inches in length, with an inner diameter of from about 0.22 inches to about 0.31 inches and an outer diameter of about 0.25 inches to about 0.35 inches. Preferably, the second telescoping cylinder 282 is from about 0.23 inches to about 0.27 inches in length, with an inner diameter of from about 0.24 inches to about 0.29 inches and an outer diameter of about 0.27 inches to about 0.33 inches. More preferably, the second telescoping cylinder 282 is about 0.25 inches in length, with an inner diameter of about 0.27 inches and an outer diameter of about 0.3 inches.

As illustrated in FIGS. 14–16, a spring 284 biases the first and second telescoping cylinders 280 and 282 towards a position in which the first telescoping cylinder 280 and the second telescoping cylinder 282 are extended from the outer cylinder 242.

An alternative embodiment of the bone anchor implantation device 310 is shown in FIGS. 17–20.

Figure 17:
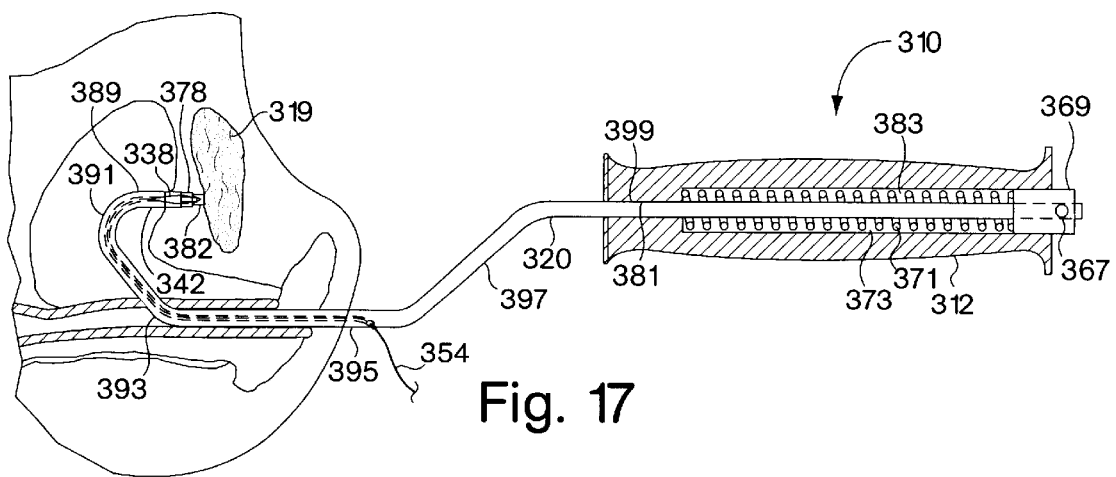
FIG. 17 is a schematic view showing the interior structure of the handle an alternate embodiment of the bone anchor implantation device inserted into the vagina with the proximal end of the second telescoping cylinder contacting the pubic bone.
Figure 18:
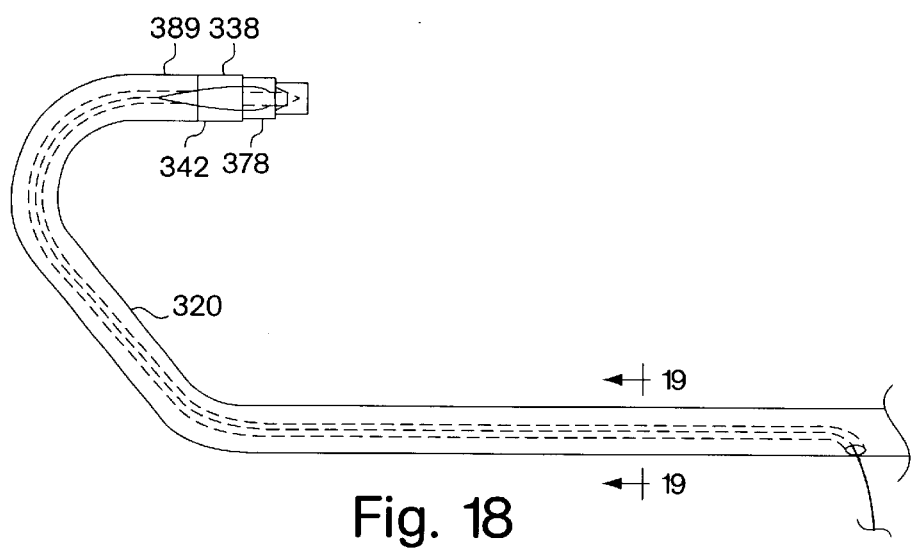
FIG. 18 is an enlarged view of the shaft of the alternate embodiment of the bone anchor implantation device illustrated in FIG. 17.

As illustrated in FIGS. 17 and 18, the shaft 320 has a generally straight proximal section 399, a first generally bent section 397, a generally straight median section 395, a second bent section 393, a generally curved section 391, and a distal generally straight section 389.

The straight proximal section 399 may be from about 3.0 inches to about 6.0 inches in length. Preferably, the straight proximal section 399 is from about 4.0 inches to about 5.0 inches in length. More preferably, the straight proximal section 399 is about 4.5 inches in length.

The first bent section 397 may be from about 1.0 inches to about 3.0 inches in length. Preferably, the first bent section 397 is from about 1.5 inches to about 2.5 inches in length. More preferably, the first bent section 397 is about 2 inches in length.

The first bent section 397 may bend at an angle of from about 35° to about 55° relative to the straight proximal section 399. Preferably, the first bent section 397 bends at an angle of from about 40° to about 50° relative to the straight proximal section 399. More preferably, the first bent section 397 bends at an angle of about 45° relative to the straight proximal section 399.

The straight median section 395 may be from about 2 inches to about 4 inches in length. Preferably, the straight median section 395 is from about 2.5 inches to about 3.5 inches in length. More preferably, the straight median section 395 is about 3 inches in length.

The second bent section 393 may be from about 0.5 inches to about 2.5 inches in length. Preferably, the second bent section 393 is from about 1.0 inches to about 2.0 inches in length. More preferably, the second bent section 393 is about 1.5 inches in length.

The second bent section 393 may bend at an angle of from about 125° to about 145° relative to the straight median section 395. Preferably, the second bent section 393 bends at an angle of from about 130° to about 140° relative to the straight median section 395. More preferably, the second bent section 393 bends at an angle of about 135° relative to the straight median section 395.

The curved section 391 may curve through an arc of from about 70° to about 110° with a radius from about 0.2 inches to about 0.6 inches. Preferably, the curved section curves 391 through an arc of from about 80° to about 100° with a radius from about 0.3 inches to about 0.5 inches. More preferably, the curved section 391 curves through an arc of about 90° with a radius of 0.4 inches.

The distal straight section 389 may be from about 0.5 inches to about 0.9 inches in length. Preferably, the distal straight section 389 is from about 0.6 inches to about 0.8 inches in length. More preferably, the distal straight section 389 is about 0.7 inches in length.

The shaft 320 has a lumen extending therethrough. The lumen may have a diameter from about 0.03 inches to about 0.07 inches and the shaft 320 may have an outer diameter from about 0.2 inches to about 0.3 inches. Preferably, the lumen has a diameter from about 0.04 inches to about 0.06 inches and the shaft 320 has an outer diameter from about 0.24 inches to about 0.26 inches. More preferably, the lumen has a diameter of about 0.05 inches and the shaft 320 has an outer diameter of about 0.250 inches.

Figure 19:
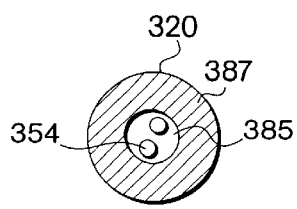
FIG. 19 is a cross sectional view of the shaft of the bone anchor implantation device shown in FIG. 18 taken along line 19—19 of FIG. 18.

Preferably, the shaft 320 has an insert 387 therein with a lumen 385 extending therethrough as best illustrated in the cross section of FIG. 19. The insert 387 may be made of a variety of materials such as stainless steel or plastic.

The insert 387 has an outer diameter approximately. that of the diameter of the lumen in the shaft such that the insert 387 fits snugly within the lumen of the shaft. The insert 387 may have an outer diameter from about 0.2 inches to about 0.3 inches. Preferably, the insert 387 has an outer diameter from about 0.21 inches to about 0.27 inches. More preferably, the insert 387 has an outer diameter of about 0.23 inches.

The insert 387 has a lumen 385 extending therethrough having a diameter large enough to accommodate a suture 354. The diameter of the lumen 385 may be from about 0.02 inches to about 0.100 inches. Preferably, the diameter of the lumen 385 is from about 0.04 inches to about 0.08 inches. More preferably, the diameter of the lumen 385 is about 0.06 inches.

Figure 20:
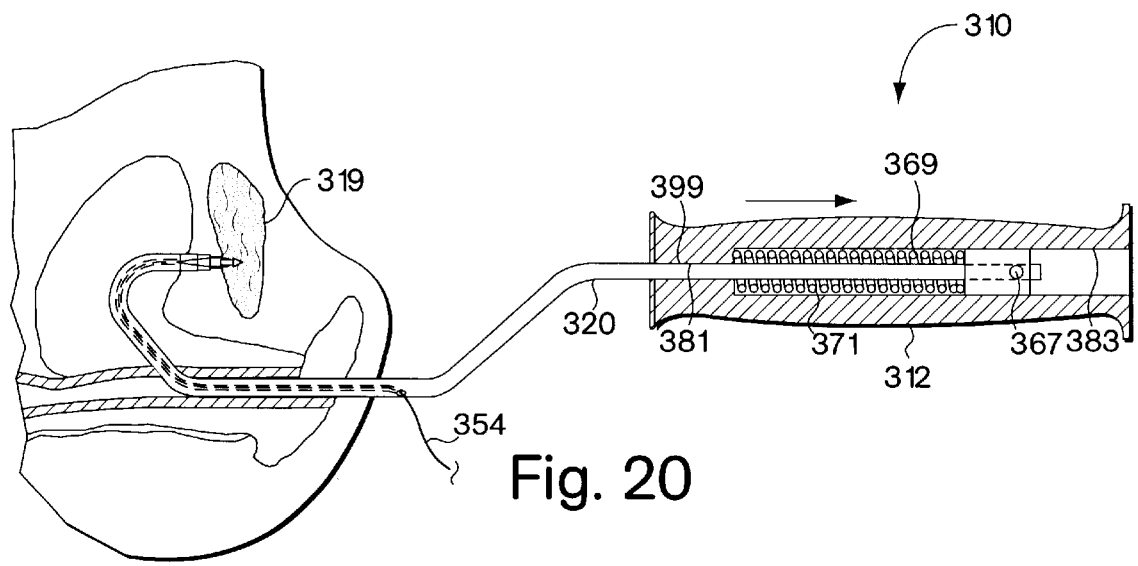
FIG. 20 is a schematic view showing the interior structure of the handle of an alternate embodiment of the bone anchor implantation device illustrated in FIG. 17 inserted into the vagina showing the implantation of a bone anchor into the pubic bone and the compression of the spring.

As illustrated in FIGS. 17, 18 and 20, the shaft 320 has a bore therein which is large enough to permit the suture 354 to exit from the shaft 320. In the embodiment shown in FIGS. 17, 18 and 20, the bore is located in the straight median section 395 at a position in which it is located outside of the patient's body when the bone anchor 348 has been inserted into the patient's bone. However, those skilled in the art will appreciate that the bore may be located in other locations such as the first bent section 397.

As illustrated in FIGS. 17 and 20, the shaft 320 extends through a lumen 383 in the handle 312. The lumen 383 has a narrow distal section 381 having a diameter slightly larger thin the outer diameter of the shaft 320 and a wider proximal section 373 adapted to receive a spring 371.

The shaft 320 passes through the interior of the spring 371 as depicted in FIGS. 17 and 20. The distal end of the spring 371 contacts the distal end of the wider proximal section 373 of the lumen. The proximal end of the spring contacts a plug 369. The plug 369 has a lumen through which the shaft 320 passes and a bore adapted to receive a screw 367. The screw 367 passes through the bore in the plug 369 and a bore in the shaft 320 which is aligned with the bore in the plug, thereby securing the shaft 320 to the plug 369.

The resistance of the spring 371 is selected to be equal to the force with which the bone anchor 348 is to be driven into the bone. For example, where the bone anchor 348 is to be driven into the bone by applying 20 pounds of force, the spring 371 is a 20 pound spring. The spring indicates when the desired amount of force has been applied because the user can sense when the spring has been completely compressed.

The spring 371 may have a resistance of from about 5 to about 35 pounds. Preferably, the spring 371 has a resistance from about 15 to about 25 pounds. More preferably, the spring 371 has a resistance of 20 pounds.

Those skilled in the art will appreciate that the anchor implantation device shown in FIGS. 13–16 may also be adapted to include a force indicating spring in the handle.

As illustrated in FIGS. 17, 18 and 20, a bone anchor mount 338 and a protective sheath 378 as described above with respect to the embodiment of FIGS. 13–16 are attached to the end of the distal straight section 389.

The hooked bone anchor implantation devices 210, 310 are used as follows. An incision in the anterior vaginal wall is made as described above. The site for bone anchor implantation is located by palpation as described above.

Figure 21:
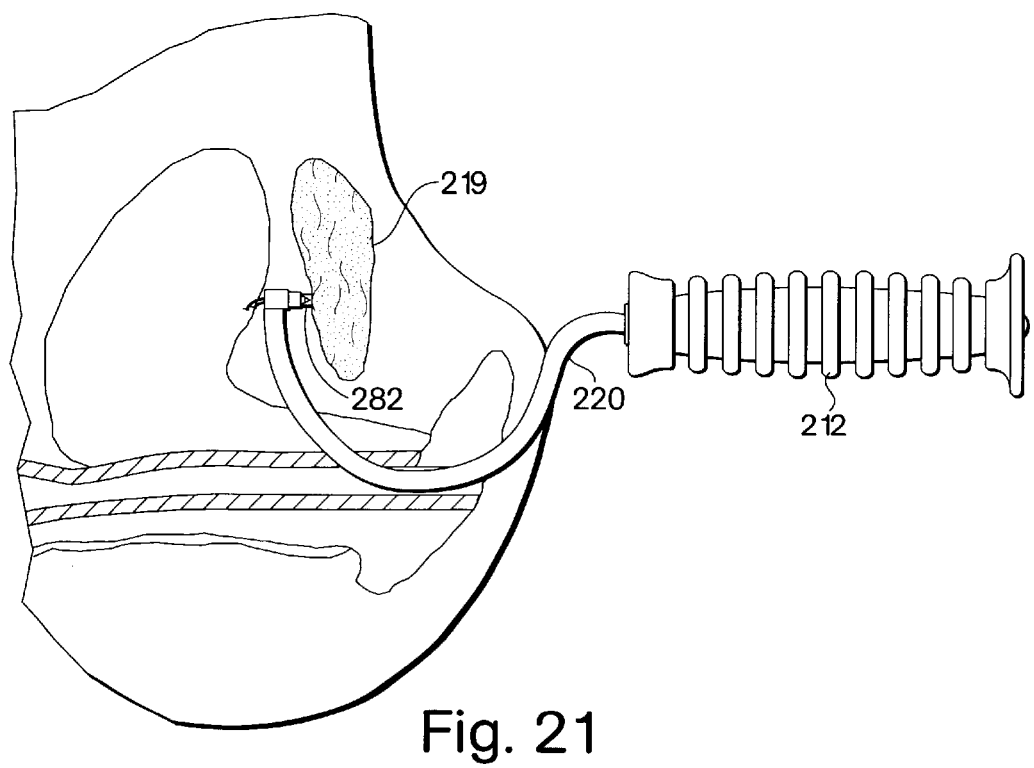
FIG. 21 is a side view of the bone anchor implantation device of FIG. 13 showing a protective sheath contacting the pubic bone.
Figure 22:
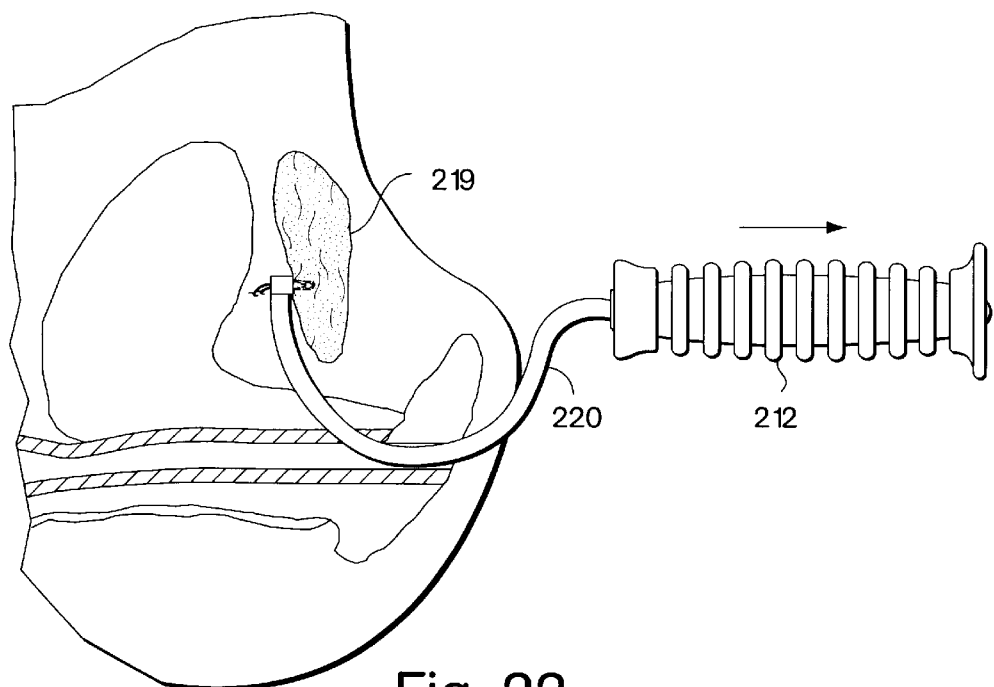
FIG. 22 is a side view of the bone anchor implantation device of FIG. 13 showing the bone anchor implanted into the pubic bone.
Figures 23, 24:
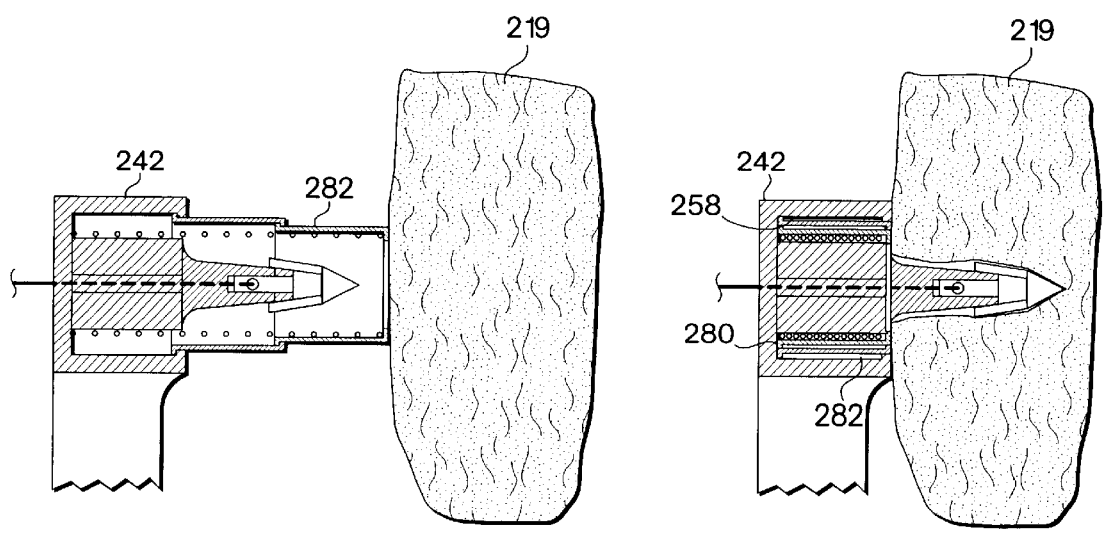
FIG. 23 is a cross sectional view of the bone anchor mount and protective sheath when the protective sheath is contacting the pubic bone.
FIG. 24 is a cross sectional view of the bone anchor mount and the protective sheath when the bone anchor is being implanted into the pubic bone.

The hooked bone anchor implantation device 210, 310 is inserted into the vagina as shown in FIGS. 17 and 21 with the patient in the lithotomy position and the surgeon located between the patient's legs. The shaft 220, 320 is inserted through the incision and the and the protective sheath 278, 378 is positioned such that the proximal end of the second telescoping cylinder 282, 382 contacts the pubic bone 219, 319 as shown in FIGS. 17, 21, and 23. At this time, the first and second telescoping cylinders 280, 380, 282, 382 are biased to a position in which they extend from the outer cylinder 242, 342 to cover the bone anchor. The bone anchor is inserted into the bone by applying a retrograde force to the bone anchor. The retrograde force can be applied in a number of ways as will be apparent to one of skill in the art. Preferably, the bone anchor is implanted by pulling the handle. For example, the handle may be pulled in a retrograde direction (toward the user) to implant the anchor as shown in FIGS. 20 and 22. As the device is pulled in a retrograde motion, the first and second telescoping cylinders 280, 282, 380, 382 retract inside the cavity 258, 358 of the outer cylinder as shown in FIGS. 20, 22 and 24 and the bone anchor 248, 348 is driven into the pubic bone 219, 319. Because the patient's body weight provides an opposing force, the user need only apply a small amount of force, such as 10–20 pounds, in order to drive the bone anchor 248, 348 into the bone 219, 319. The device 210, 310 is then pushed away from the implanted anchor to disengage the device from the anchor. The device is then removed from the vagina, leaving the bone anchor 248, 319 in the bone 219, 319 with the suture extending therefrom. The bladder neck is then compressed, suspended or stabilized using the suture (s) extending from the bone anchor(s) as described above.

As shown in FIG. 20, in the device 310 having a spring 371 inside the handle 312, the spring 371 is compressed when the handle is pulled in a retrograde direction to drive the bone anchor into the bone. In this embodiment, the user can detect when the spring 371 has been completely compressed, or compressed by a predetermined amount, indicating that the desired amount of force for driving the bone anchor into the bone has been applied.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims.

What is claimed is:

1. A method for inserting a bone anchor coupled to a suture releasably engaged to a hook-shaped bone anchor implantation device into a bone comprising the steps of:

providing a bone anchor inserter, comprising:
- a handle including a proximal end, a distal end, and a longitudinal axis;
- a hook shaped shaft including a first end and a second end, the first end being connected to the handle;
- a tapered bone anchor mount for releasably engaging the bone anchor coupled to a suture connected to the second end of the shaft, the bone anchor mount comprising an outer cylinder, and a tapered bone anchor receptacle, wherein the tapered bone anchor mount includes a longitudinal axis and the longitudinal axis of the tapered bone anchor mount is aligned with the longitudinal axis of the handle; and
- a protective sheath connected to the bone anchor mount for isolating the bone anchor prior to implantation of the bone anchor into bone, locating a bone anchor implantation site; and implanting the bone anchor into the bone by applying a retrograde force to the bone anchor insertor substantially along the longitudinal axis of the handle.

2. The method of claim 1, wherein the providing a bone anchor inserter step further comprises providing a bone anchor inserter in which the outer cylinder comprises a cavity therein and an inner cylinder is connected to the outer cylinder within the cavity.

3. The method of claim 1, wherein the providing a bone anchor inserter step further comprises providing a bone anchor inserter in which the outer cylinder comprises a distal end and a proximal end, the outer cylinder also comprising an annular shoulder at the proximal end.

4. The method of claim 1, wherein the providing a bone anchor inserter step further comprises providing a bone anchor inserter in which the bone anchor receptacle comprises at least one groove adapted to accommodate the suture.

5. The method of claim 2, wherein the providing a bone anchor inserter step further comprises providing a bone anchor inserter in which the inner cylinder includes at least one groove adapted to accommodate the suture.

6. The method of claim 1, wherein the providing a bone anchor inserter step further comprises providing a bone anchor inserter in which the shaft includes a lumen, adapted to accommodate the suture.

7. The method of claim 1, wherein the implanting step comprises the step of applying retrograde force to the bone anchor insertor to translate the retrograde force to the bone anchor.

8. The method of claim 1, wherein the locating and implanting steps are accomplished transvaginally.

9. The method of claim 1, wherein at least one bone anchor couple to a suture is implanted transvaginally into a pubic bone of a patient.

10. The method of claim 9, wherein said at least one bone anchor couple to a suture is implanted into the interior surface of the pubic bone.

11. The method of claim 9, wherein said at least one bone anchor couple to a suture is implanted in the pubic bone on either side of the urethra.

12. The method of claim 10, at said least one bone anchor couple to a suture is implanted lateral to the symphysis pubis and cephalad to the inferior edge of the pubic bone.

13. The method of claims 12, further comprising stabilizing the bladder neck with the suture attached to the bone anchor.

14. The method of claim 12, further comprising:
- creating an opening in the tissue between the vaginal wall and the urethra;
- positioning a sling in the opening; and
- stabilizing the bladder neck with the sling using sutures connected between the sling and the bone anchors.

* * * * *